(12) United States Patent
McGinley et al.

(10) Patent No.: US 11,517,331 B2
(45) Date of Patent: Dec. 6, 2022

(54) INSTRUMENT LEADING EDGE MEASUREMENT SYSTEM AND METHOD

(71) Applicant: McGinley Engineered Solutions, LLC, Casper, WY (US)

(72) Inventors: Joseph C. McGinley, Casper, WY (US); Lawson Fisher, Palo Alto, CA (US)

(73) Assignee: McGinley Engineered Solutions, LLC, Casper, WY (US)

( * ) Notice: Subject to any disclaimer, the term of this patent is extended or adjusted under 35 U.S.C. 154(b) by 302 days.

(21) Appl. No.: 16/939,844

(22) Filed: Jul. 27, 2020

(65) Prior Publication Data

US 2021/0085343 A1    Mar. 25, 2021

Related U.S. Application Data

(63) Continuation of application No. 14/845,602, filed on Sep. 4, 2015, now Pat. No. 10,758,250.

(Continued)

(51) Int. Cl.
*A61B 17/17* (2006.01)
*A61B 17/16* (2006.01)
(Continued)

(52) U.S. Cl.
CPC .............. *A61B 17/17* (2013.01); *A61B 17/15* (2013.01); *A61B 17/164* (2013.01); *A61B 17/1622* (2013.01); *A61B 17/1626* (2013.01); *A61B 17/1637* (2013.01); *A61B 90/06* (2016.02); *A61B 2017/00022* (2013.01); *A61B 2090/062* (2016.02)

(58) Field of Classification Search
CPC .. A61B 17/16; A61B 17/1626; A61B 17/1622
USPC .......................................................... 606/80
See application file for complete search history.

(56) References Cited

U.S. PATENT DOCUMENTS 1,831,813 A    11/1931   Levedahl
2,883,891 A    4/1959    Robinson et al.
(Continued)

FOREIGN PATENT DOCUMENTS

DE    102011056927 A1    6/2013
WO         9724991 A1    7/1997
(Continued)

*Primary Examiner* — Matthew J Lawson
(74) *Attorney, Agent, or Firm* — Holzer Patel Drennan

(57) ABSTRACT

Measurement of a leading edge of an instrument passing from a first medium having a first density to a second medium having a second density using a displacement sensor alone. In particular, a displacement signal, a velocity signal, and an acceleration signal measured from or derived from a displacement sensor are analyzed to determine when the leading edge of the instrument passes from the first material to the second material as the leading edge of the instrument is advanced relative to the material. For instance, the measurement may be used to output an occurrence signal that indicates to a user that the instrument has passed from the first medium to the second medium. Additionally, a length measurement of the path of the instrument when passing from the first medium to the second medium may be recorded, and/or the instrument may be controlled (e.g., the instrument may be stopped).

13 Claims, 34 Drawing Sheets

Related U.S. Application Data

(60) Provisional application No. 62/046,468, filed on Sep. 5, 2014.

(51) Int. Cl.
*A61B 90/00* (2016.01)
*A61B 17/15* (2006.01)
*A61B 17/00* (2006.01)

(56) References Cited

U.S. PATENT DOCUMENTS

| | | |
|---|---|---|
| 3,804,544 A | 4/1974 | Adams |
| 4,014,621 A | 3/1977 | Johnson et al. |
| 4,063,356 A | 12/1977 | Hepworth |
| 4,157,231 A | 6/1979 | Phillips |
| 4,310,269 A | 1/1982 | Neu et al. |
| 4,329,092 A | 5/1982 | Ponitzsch et al. |
| 4,329,095 A | 5/1982 | Schmuck |
| 4,644,335 A | 2/1987 | Wen |
| 4,710,075 A | 12/1987 | Davison |
| 4,723,911 A | 2/1988 | Kurtz |
| 4,765,333 A | 8/1988 | Bray |
| 4,867,158 A | 9/1989 | Sugg |
| 4,951,690 A | 8/1990 | Baker |
| 5,013,194 A | 5/1991 | Weinhold |
| 5,014,793 A | 5/1991 | Germanton et al. |
| 5,022,798 A | 6/1991 | Eckman |
| 5,071,293 A | 12/1991 | Wells |
| 5,133,728 A | 7/1992 | Petersen |
| 5,139,376 A | 8/1992 | Pumphrey |
| 5,161,921 A | 11/1992 | Corsi |
| 5,277,799 A | 1/1994 | Bransch |
| 5,361,504 A | 11/1994 | Huang |
| 5,380,333 A | 1/1995 | Meloul et al. |
| 5,411,503 A | 5/1995 | Hollstein et al. |
| 5,533,842 A | 7/1996 | Johnson et al. |
| 5,538,423 A | 7/1996 | Coss et al. |
| 5,584,838 A | 12/1996 | Rona et al. |
| 5,599,142 A | 2/1997 | Fujimoto et al. |
| 5,613,810 A | 3/1997 | Bureller |
| 5,810,828 A | 9/1998 | Lightman et al. |
| 5,902,306 A | 5/1999 | Norman |
| 5,961,257 A | 10/1999 | Bettini et al. |
| 5,980,248 A | 11/1999 | Kusakabe et al. |
| 6,033,409 A * | 3/2000 | Allotta .............. B25F 5/003 606/80 |
| 6,081,741 A | 6/2000 | Hollis |
| 6,096,042 A | 8/2000 | Herbert |
| 6,342,057 B1 | 1/2002 | Brace et al. |
| 6,494,590 B1 | 12/2002 | Paganini |
| 6,527,778 B2 | 3/2003 | Athanasiou et al. |
| 6,587,184 B2 | 7/2003 | Wursch et al. |
| 6,665,948 B1 | 12/2003 | Kozin et al. |
| 6,786,683 B2 | 9/2004 | Schaer et al. |
| 6,925,725 B2 | 8/2005 | Herrmann et al. |
| 7,073,989 B2 | 7/2006 | Erickson et al. |
| 7,185,998 B2 | 3/2007 | Oomori |
| 7,220,088 B2 | 5/2007 | Ferrari et al. |
| 7,235,940 B2 | 6/2007 | Bosch et al. |
| 7,314,048 B2 | 1/2008 | Couture et al. |
| 7,482,819 B2 | 1/2009 | Wuersch |
| 7,578,642 B2 | 8/2009 | Fritsche et al. |
| 7,681,659 B2 | 3/2010 | Zhang et al. |
| 7,691,106 B2 | 4/2010 | Schenberger |
| 7,840,253 B2 | 11/2010 | Tremblay |
| 7,946,049 B1 | 5/2011 | Wilton |
| 7,992,311 B2 | 8/2011 | Cerwin |
| 8,092,457 B2 | 1/2012 | Oettinger |
| 8,162,074 B2 | 4/2012 | Cook |
| 8,167,518 B2 | 5/2012 | Mathis et al. |
| 8,171,642 B2 | 5/2012 | Fritsche |
| 8,317,437 B2 | 11/2012 | Merkley et al. |
| 8,460,297 B2 | 6/2013 | Watlington |
| 8,511,945 B2 | 8/2013 | Apkarian |
| 8,734,153 B2 | 5/2014 | Arzanpour |
| 8,821,493 B2 | 9/2014 | Anderson |
| 8,894,654 B2 | 11/2014 | Anderson |
| 8,925,169 B2 | 1/2015 | Schevers |
| 8,970,207 B2 | 3/2015 | Baumgartner |
| 9,022,949 B2 | 5/2015 | Herndon |
| 9,114,494 B1 | 8/2015 | Mah |
| 9,204,885 B2 | 12/2015 | McGinley |
| 9,358,016 B2 | 6/2016 | McGinley |
| 9,370,372 B2 | 6/2016 | McGinley |
| 9,492,181 B2 | 11/2016 | McGinley |
| 9,855,060 B2 | 1/2018 | Ardel |
| 2001/0031919 A1 | 10/2001 | Strommer |
| 2001/0047219 A1 | 11/2001 | Oden |
| 2002/0165549 A1 | 11/2002 | Owusu-Akyaw et al. |
| 2003/0049082 A1 | 3/2003 | Morrison |
| 2003/0229351 A1 | 12/2003 | Tidwell |
| 2004/0146367 A1 | 7/2004 | Gerhardt |
| 2004/0179829 A1 | 9/2004 | Phillips et al. |
| 2004/0215395 A1 | 10/2004 | Strasser |
| 2005/0116673 A1 * | 6/2005 | Carl ................. A61B 17/1626 318/432 |
| 2005/0131415 A1 * | 6/2005 | Hearn ................. B25B 23/147 606/80 |
| 2005/0169717 A1 | 8/2005 | Field |
| 2005/0261870 A1 | 11/2005 | Cramer |
| 2006/0004371 A1 | 1/2006 | Williams et al. |
| 2006/0008771 A1 | 1/2006 | Courvoisier |
| 2006/0025677 A1 | 2/2006 | Verard |
| 2006/0074292 A1 | 4/2006 | Thomson |
| 2006/0241628 A1 | 10/2006 | Parak |
| 2006/0258938 A1 | 11/2006 | Hoffman |
| 2007/0030486 A1 | 2/2007 | Gelbart |
| 2007/0035311 A1 | 2/2007 | Wuersch |
| 2007/0041799 A1 | 2/2007 | Schaefer |
| 2008/0119725 A1 | 5/2008 | Lloyd |
| 2008/0167653 A1 | 7/2008 | Watlington |
| 2008/0226409 A1 | 9/2008 | Hasenzahl |
| 2008/0228195 A1 | 9/2008 | von Jako |
| 2008/0243125 A1 | 10/2008 | Guzman |
| 2008/0292416 A1 | 11/2008 | Kado et al. |
| 2009/0131986 A1 | 5/2009 | Lee et al. |
| 2009/0182226 A1 | 7/2009 | Weitzner |
| 2009/0245956 A1 | 10/2009 | Apkarian et al. |
| 2009/0299439 A1 | 12/2009 | Mire et al. |
| 2009/0326537 A1 | 12/2009 | Anderson |
| 2010/0114099 A1 | 5/2010 | Patwardhan |
| 2010/0137874 A1 | 6/2010 | Kim et al. |
| 2010/0239380 A1 | 9/2010 | Amirov et al. |
| 2011/0020084 A1 | 1/2011 | Brett |
| 2011/0060242 A1 | 3/2011 | Hausman |
| 2011/0245831 A1 | 10/2011 | Giersch et al. |
| 2011/0245832 A1 | 10/2011 | Giersch et al. |
| 2011/0245833 A1 | 10/2011 | Anderson |
| 2011/0256496 A1 * | 10/2011 | Arzanpour ........... A61C 1/0007 433/27 |
| 2011/0301611 A1 | 12/2011 | Garcia |
| 2012/0037386 A1 | 2/2012 | Cook |
| 2012/0123418 A1 | 5/2012 | Giurgi |
| 2012/0179070 A1 | 7/2012 | Pommer et al. |
| 2012/0253348 A1 | 10/2012 | Arlettaz et al. |
| 2013/0122466 A1 | 5/2013 | Connor |
| 2013/0237811 A1 | 9/2013 | Mihailescu |
| 2013/0304069 A1 | 11/2013 | Bono et al. |
| 2013/0307529 A1 | 11/2013 | Baumgartner |
| 2013/0327552 A1 | 12/2013 | Lovelass |
| 2014/0039517 A1 | 2/2014 | Stryker |
| 2014/0081659 A1 | 3/2014 | Nawana |
| 2014/0107471 A1 | 4/2014 | Haider |
| 2014/0275760 A1 | 9/2014 | Lee |
| 2014/0275989 A1 | 9/2014 | Jacobsen |
| 2014/0350685 A1 | 11/2014 | Bagga et al. |
| 2015/0066030 A1 | 3/2015 | McGinley |
| 2015/0066035 A1 | 3/2015 | McGinley |
| 2015/0066036 A1 | 3/2015 | McGinley |
| 2015/0066037 A1 | 3/2015 | McGinley |
| 2015/0066038 A1 | 3/2015 | McGinley et al. |
| 2015/0165580 A1 | 6/2015 | Holland |
| 2016/0120553 A1 | 5/2016 | Xie |
| 2016/0247276 A1 | 8/2016 | Chou |

(56) References Cited

U.S. PATENT DOCUMENTS

| | | |
|---|---|---|
| 2017/0143396 A1 | 5/2017 | McGinley |
| 2017/0345398 A1 | 11/2017 | Fuchs |
| 2018/0070113 A1 | 3/2018 | Phillips |
| 2018/0110572 A1 | 4/2018 | Flatt |
| 2018/0260931 A1 | 9/2018 | Ozguner |
| 2019/0209287 A1 | 7/2019 | Zenz-Olson |
| 2019/0254684 A1 | 8/2019 | McGinley |
| 2019/0254685 A1 | 8/2019 | McGinley |

FOREIGN PATENT DOCUMENTS

| | | |
|---|---|---|
| WO | 2015006296 A1 | 1/2015 |
| WO | 2015034562 A1 | 3/2015 |
| WO | 2015014771 A3 | 4/2015 |
| WO | 2016207628 A1 | 12/2016 |

\* cited by examiner

BICORTICAL DRILL PATH

UNICORTICAL DRILL PATH

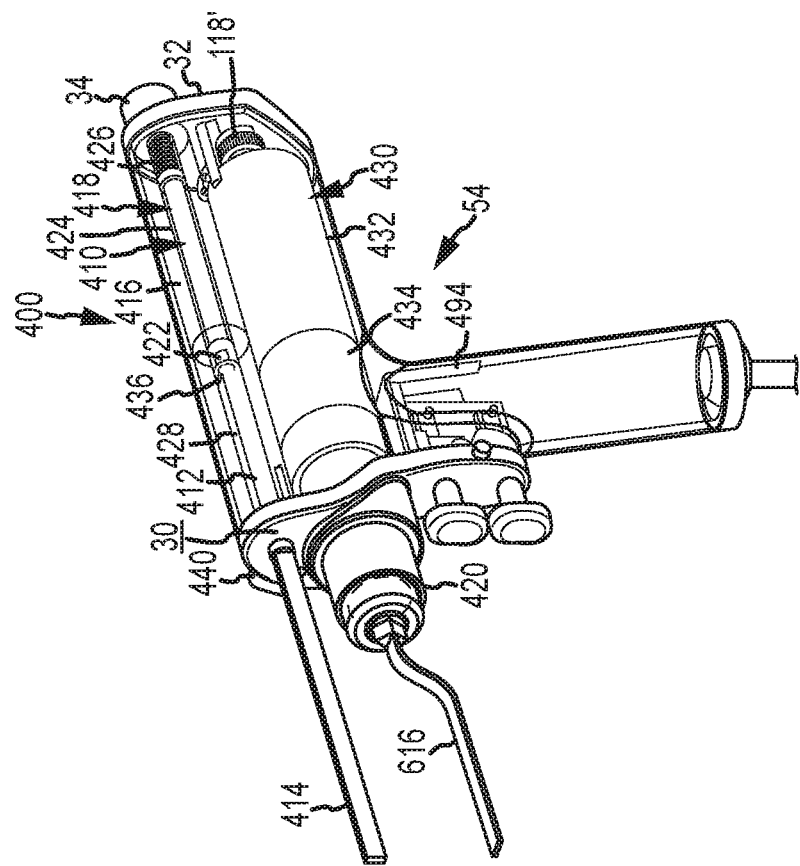
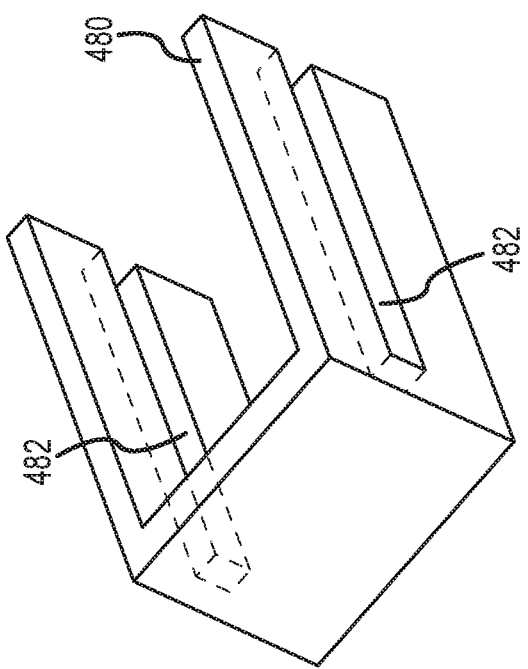
FIG. 27

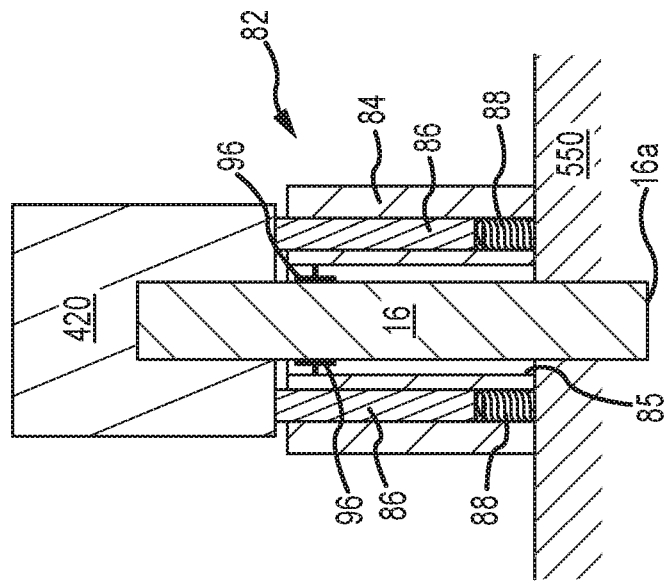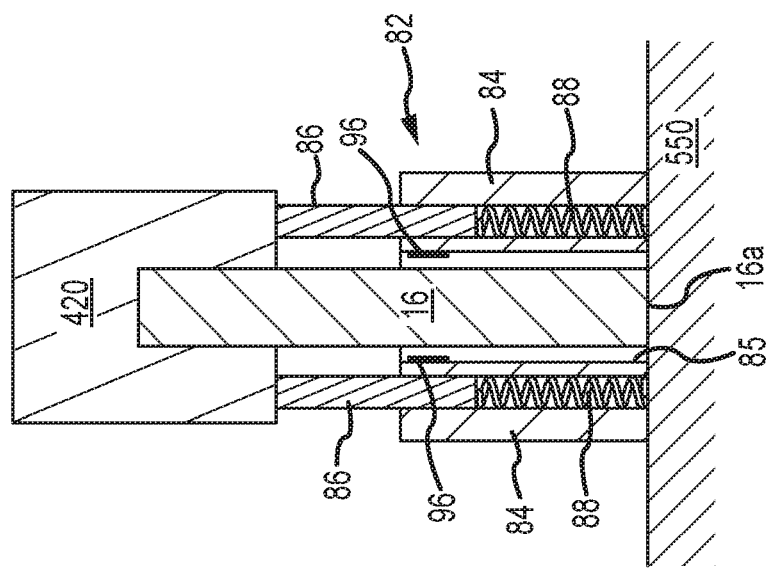

INSTRUMENT LEADING EDGE MEASUREMENT SYSTEM AND METHOD

RELATED APPLICATIONS

This application is a continuation of U.S. application Ser. No. 14/845,602, filed on Sep. 4, 2015, titled "INSTRUMENT LEADING EDGE MEASUREMENT SYSTEM AND METHOD,", which claims the benefit of U.S. Provisional Application No. 62/046,468 filed Sep. 5, 2014, entitled "INSTRUMENT LEADING EDGE MEASUREMENT SYSTEM AND METHOD," the contents of which are incorporated by reference herein as if set forth in full.

FIELD

The present disclosure relates generally to systems, methods, and apparatuses for use in connection with determining when a leading edge of an instrument passes through an interface between materials having different densities as the instrument is advanced relative to the medium. Particularly, the present disclosure facilitates providing an alert or other response to a user of an instrument when it is determined that a leading edge of an instrument (e.g., a drill bit, saw blade, etc.) passes from a first medium having a first density to a second medium having a second density. Additionally or alternatively, an alert or other response may occur at certain other occurrences. For example, the surgical instrument may be controlled in response to the instrument passing through the materials with different mediums, and/or the displacement of the instrument may be recorded.

BACKGROUND

Oftentimes in surgical procedures a powered surgical instrument such as a drill, saw, reamer, or the like, is used on a bone of a patient. As such, a surgeon may be tasked with determining, based on feel alone, when the instrument passes through the bone of the patient. Furthermore, once the instrument has been passed through the bone of the patient, it may be desirable to provide a measure of the displacement of the leading edge of the instrument relative to a reference point when the leading edges passes from a first medium having a first density to a second medium having a second density (e.g., when the leading edge of the surgical instrument passes completely through the bone). Traditional approaches of determining such displacements may require removal of the instrument from the bone and/or use of a separate depth gauge tool.

One particular context in which determining the displacement of an instrument passing through a bone is important is in the context of drilling holes in bone for placement of screws, pins, or the like. Following traumatic injury, plate and screw placement relative to a bone may be critical for adequate repair. As such, inadequate and inaccurate depth measurement following orthopedic drilling procedures may result in incorrect screw lengths, which can lead to surgical complications such as device instability, damage to anatomic structures, or device failure. Furthermore, placement of pins (e.g., transcutaneous pins) may require accurate placement of the distal end of the pin relative to a bone structure (e.g., into a hard outer cortex of the bone).

Another context in which determining when an instrument passes from a first medium to a second medium is advantageous concerns determining completion of an operation using an instrument. For example, whether sawing, drilling, reaming, or performing some other powered operation relative to bone, upon the completion of the operation (i.e., upon passing completely through the bone or into a specific layer of the bone), the operation is preferably arrested to prevent damage to surrounding tissue by the powered instrument. Currently such termination of the operation largely is the responsibility of a surgeon using feel alone to determine an operation has completed.

However, determining when an instrument passes through a bone may be complicated because of the anatomical structure of the bone. For instance, as shown in FIGS. 1A, 1B, and 1C, the bony structure of the human anatomy consists mainly of cortical bone 10 having a hard outer cortex 12 and a soft inner medullary layer 14. As described above, oftentimes powered instruments are used in relation to the bone, which, given the hard nature of bone, may be difficult to operate on using hand operated tools. With the ease of powered instruments also comes difficulty in terminating operation of the instrument once the operation on the bone has been terminated and/or determining a depth of an operation relative to a bone.

For example, as shown in FIG. 1A, when using a rotating drill bit 16 to form a bicortical bore 18 through the cortical bone 10, the rotating drill bit 16 passes through a first portion 12a of the hard outer cortex 12, a soft non-resistant medullary layer 14, and a second portion 12b of the hard outer cortex 12. However, as shown in FIG. 1B, when using a rotating drill bit 16 to form a unicortical bore 20 through the cortical bone 10, the rotating drill bit 16 passes through an entry point 22a of the hard outer cortex 12 and an exit point 22b of the hard outer cortex 12 a first portion 12a without penetrating the soft non-resistant medullary layer 14. Furthermore, in FIG. 1C, an instrument (e.g., a saw blade 130 having a blade edge 132) may pass through the entirety of the bone. As such, the saw blade edge 132 may pass through a first portion 134 of the bone 10 comprising only a first portion 12a of the hard outer cortex 12, a second portion 136 of the bone 10 comprising both hard outer cortex 12 and the soft medullary layer 14, and a third portion 138 of the bone 10 comprising only of a second portion 12b of the hard outer cortex 12. In this regard, each of the first portion 134, second portion 136, and the third portion 138 may have interfaces at which the perceived density of the medium changes. Further still, each of the portions 134, 136, and 138 may exhibit substantially the same density as the hard outer cortex 12 may be subjected to the instrument in all portions. Thus, variables such as the relative thickness of the hard outer cortex 12 and soft medullary layer 14, whether the operation is unicortical or bicortical, and/or the relative amount of hard outer cortex 12 and medullary layer 14 subjected to the instrument may affect the ability of the user to sense when the leading edge of the instrument passes through the relative portions of the bone 10. In any regard, in all these examples a surgeon may be required to determine when the drill bit passes through the bone by feel alone. As can be appreciated, in each context described in FIGS. 1A-1C, the feel demonstrated by the instrument may differ. As such, consistently determining a depth of an operation using a powered instrument relative to the bone 10 may be difficult. That is, the determination of when the drill bit has passed through a portion of or the entirety of the bone may require skill by the surgeon and may not be repeatable for all bones of all patients. In the event the surgeon does not cease an operation of the powered instrument upon completion of the operation, surrounding tissue or other structures may be damaged.

As such, a possible resulting complication of an operation using a powered instrument is that the surgeon may not precisely "feel" the instrument pass through a desired portion of the bone, thereby possibly damaging tissue adjacent to the bone or resulting in the instrument not passing into a desired portion of the bone. Another complication may occur if the depth of a bore or cut is not properly measured. For instance, if using a depth gage, the depth gage may be improperly placed or the gage may be grasped prior to passing the distal end of the bore. In either regard, a depth measurement may be determined that is smaller or larger than the true depth. Accordingly, current techniques to operations using powered instruments on a patient may be inefficient, thus adding cost and the potential for adverse complications to the operation.

SUMMARY

In this regard, the present disclosure is generally related to improved systems and methods related to a measurement system for an instrument. Specifically, the present disclosure is related to embodiments of measurement systems that may detect when a leading edge of a powered instrument passes from a first medium having a first density to a second medium having a second density. The powered instrument with which the measurement system described herein is used may include a surgical instrument such as, for example, a surgical drill, a surgical saw, a surgical reamer, or the like. However, applications beyond the surgical context are contemplated such that the techniques described herein may be used in other contexts where a powered instrument is used to perform an operation (e.g., cutting, sawing, drilling, grinding, reaming, etc.) relative to a structure having at least a first layer with a first density and a contiguous second layer with a second density. Examples may include uses with construction power tools, oil and gas drilling operations, etc.

The present disclosure is particularly directed to a measurement system for detection of when a leading edge of an instrument passes from a first medium to a second medium with the use of a single sensor alone. In an embodiment, the single sensor may be a displacement sensor. In this regard, techniques have been proposed such as those described in U.S. Pat. No. 6,665,948 or U.S. patent application Ser. No. 14/018,252, the entireties of which are incorporated by reference herein. However, these proposed techniques for measurement systems rely on the use of a displacement sensor in combination with a force sensor to determine when a leading edge of the instrument passes from a first medium to a second medium. Accordingly, the required use of a force sensor may result in increased complexity and cost of instruments incorporating such a measurement system. Furthermore, such applications may be difficult to retrofit or use with conventional instruments. Further still, the present inventors have recognized that varying surgical techniques often lead to differing force application during operations. Thus, force measurements may be inconsistent from user to user. In addition, some users apply forces below a threshold value measurable by certain sensors. As such, the required use of a force sensor may present difficulties.

In another embodiment, the single sensor may be an acceleration sensor. Regardless of the nature of the sensor (i.e., whether a displacement sensor or acceleration sensor), the sensor may be operative to output a signal that corresponds to a characteristic of the movement of the leading edge of an instrument relative to a reference point. For instance, in the case of a displacement sensor, the characteristic may be the displacement of the leading edge of the instrument relative to a reference point. In the case of an acceleration sensor, the characteristic may be the acceleration of the leading edge of the instrument relative to a reference point. In either regard, the present disclosure contemplates determining an occurrence of a leading edge of an instrument passing from a first medium to a second medium using only the signal corresponding to the characteristic of movement of the leading edge of the instrument relative to a reference point. By using only the signal representative of the characteristic of the movement of the leading edge, it is further contemplated that the signal output from the sensor itself may undergo processing or transformations (e.g., mathematical operations) to provide further signals used to determine the occurrence of the leading edge of the instrument passing from a first medium to a second medium all of which are derived from the measured signal of the single sensor. That is, the occurrence may be determined solely by a single sensor in the absence of any additional sensors. For instance, in the case of a displacement sensor, a displacement signal may be derived directly from the sensor. Additionally, a velocity signal and an acceleration signal may be derived directly from the displacement signal as described in greater detail below. Furthermore, in the case of an acceleration sensor, and acceleration signal may be derived directly from the sensor. Furthermore, a velocity signal and the displacement signal may be derived directly from the acceleration signal as described in greater detail below. In this regard, even when using additional signals derived from a signal that is directly output by the sensor, the occurrence of the leading edge of the instrument passing the first medium to a second medium may be determined using only a single sensor. Accordingly, in contrast to previous approaches that utilize both a displacement sensor and a force sensor, the present disclosure describes an approach utilizing a single sensor alone, which may provide reliable results without the complication of the added second sensor (e.g. without a force sensor). This may allow for a more cost-effective instrument and/or incorporation of the sensor in an instrument guide that is separate from the instrument itself, further reducing the costs of the measurement system and allowing for retrofits of existing equipment to include the measurement system. Furthermore, variations in the force applied by users do not affect the results obtained by the measurement system without use of a force sensor in the measurement. Accordingly, the measurement systems that obtain a measurement using a measurement system employing a single sensor alone may provide advantages to system employing both displacement and force sensors in combination to obtain a measurement. Furthermore, the measurements obtained by systems provided herein may provide results with accuracy similar to that achieved with the use of a force sensor in combination with a displacement sensor.

The single sensor used to determine when a leading edge of an instrument has passed through the boundary between a first medium having a first density and a second medium having a second density may be a displacement sensor or an acceleration sensor. As is discussed in greater detail below, the determination of when the leading edge of an instrument passes from a first medium to a second medium may be based on an analysis of one or more signals representing the displacement, velocity, and/or acceleration of the leading edge of the instrument. In an embodiment, a displacement sensor may be provided for outputting a displacement signal. The displacement signal may be used to determine a velocity signal (e.g. by taking a first derivative with respect to time of the displacement signal) and/or an acceleration signal (e.g., by taking a second derivative with respect to time of the displacement signal). In an embodiment, an acceleration sensor may be provided for outputting an acceleration signal. The acceleration signal may be used to determine a velocity signal (e.g., by taking a first integral with respect to time of the acceleration signal) and/or a displacement signal (e.g., by taking a second integral with respect to time of the acceleration signal).

A first aspect of the present disclosure includes a measurement system for determining when a leading edge of an instrument passes from a first medium to a second medium contiguous with the first medium, where the first medium has a first density and the second medium has a second density. The system may include a sensor that outputs a signal corresponding to a characteristic of the movement of the leading edge of the instrument relative to a reference point. The system further includes a processing module in operative communication with the sensor that is configured to determine an occurrence of the leading edge of the instrument passing from the first medium to the second medium using only the signal representative of the characteristic of the movement of the leading edge of the instrument relative to the reference point.

A number of feature refinements and additional features are applicable to the first aspect. These feature refinements and additional features may be used individually or any combination. As such, each of the following features that will be discussed may be, but are not required to be, used with any other feature or combination of features of the first aspect.

For example, the characteristic of the movement may comprise at least one of a displacement or an acceleration of the leading edge of the instrument relative to the reference point. Therefore and is addressed above, the sensor may comprise a displacement sensor or an acceleration sensor. Furthermore, in accord with the foregoing discussion regarding the determination of an occurrence of the leading edge of an instrument passing from a first medium to a second medium using only a single sensor, the determination of the occurrence may also be based on processing of the signal output by the sensor including, for example, transforms of the signal using mathematical operations. In this regard and in an embodiment, the processing module may be operative to generate a displacement signal, a velocity signal, and an acceleration signal using the signal from the sensor. Accordingly, the displacement signal, the velocity signal, and the acceleration signal may each be used to determine the occurrence of the leading edge of the instrument passing from the first medium to the second medium. It will be appreciated that in the case of a displacement sensor, the displacement signal may be provided directly from the sensor. Furthermore, in the case of acceleration sensor, the acceleration signal may be provided directly from the sensor. In any regard, the processing module may be operative to obtain or determine the displacement signal, the velocity signal, and the acceleration signal corresponding to the movement of the leading edge of the instrument for use in determining an occurrence of the instrument passing from a first medium to a second medium. For instance, the occurrence may correspond with the displacement signal, the velocity signal, and the acceleration signal all being positive simultaneously.

Furthermore and as addressed above, in various embodiments the instrument may comprise different commonly used instruments during a surgical operation. As such, in one application the instrument may be a drill and the leading edge of the instrument may include a distal end of a drill bit. In another application the instrument may be a saw and the leading edge of the instrument may include a distal end of a saw blade. In yet another application the instrument may be a drill and the leading edge of the instrument may include a distal end of a transcutaneous pin. However, the foregoing is not intended to be limiting and other applications related to powered instruments are contemplated where the leading edge of the instrument is advanced during operation of the powered instrument relative to a structure having a first medium and a contiguous second medium of different densities.

In an embodiment, the sensor may be disposed externally to the instrument. A portion of the instrument may interface with at least a portion of the sensor to produce the signal representative of the movement of the movement of the leading edge of the instrument bit relative to a reference point. For example, the sensor may be disposed in an instrument guide that is discrete and separate from the instrument itself. As may be appreciated, the instrument guide may be provided in a retrofit application where a traditional instrument is used in conjunction with the instrument guide. At least a portion of the instrument may pass through a housing of the instrument guide that includes the sensor during the operation of the instrument to determine the characteristic of the movement of the leading edge of the instrument as described above. In another embodiment, the sensor may be disposed integrally (e.g., internally) to the instrument. As such, the instrument may be a specifically configured instrument having the sensor disposed therein for use in accordance with the description provided herein.

Additionally and as contemplated above, the operation of the instrument may be a unicortical or bicortical operation. In this regard, in a unicortical operation the instrument may take a unicortical path through a bone on which the instrument is utilized. In a bicortical operation, the instrument may take a bicortical path through a bone on which the instrument is utilized. Accordingly, in an embodiment the first medium may include a first layer of bone and the second medium may comprise a second layer of bone different than the first layer. In a further embodiment, the first medium may comprise bone and the second medium may comprise a material surrounding the bone. As may be appreciated, the occurrence of the leading edge of the instrument passing from the first medium to the second medium may correspond with a number of different operations performed using an instrument relative to the bone. For instance, the present disclosure may be utilized to determine when the leading edge of an instrument enters a particular portion of the bone (e.g., when the instrument enters a hard outer cortex portion such as the hard outer cortex portion 12b described above in relation to FIG. 1A, when the instrument enters a soft medullary layer such as the medullary layer 14 described above in relation to FIG. 1A, or when the instrument exits the hard outer cortex portion into a surrounding medium such as the hard outer cortex portion 12b described above in relation to FIG. 1A). As will be described in greater detail below, different operations may benefit from determining the leading edge of an instrument passing through various ones of the interfaces between a first medium and a second medium as described above.

A second aspect includes a measurement system for determining when a leading edge of an instrument passes from a first medium to a second medium contiguous with the first medium, where the first medium has a first density and the second medium has a second density. The system may include a displacement sensor that outputs a displacement signal representative of a displacement of the leading edge of the instrument relative to a reference point. The system may also include a calculation module in operative communication with the displacement sensor for generating a velocity signal and an acceleration signal based on the displacement signal. The system may also include a processing module in operative communication with the calculation module that is configured to determine an occurrence of the leading edge of the instrument passes from the first medium to the second medium based only on the displacement signal, the velocity signal, and the acceleration signal.

A number of feature refinements and additional features are applicable to the second aspect. These feature refinements and additional features may be used individually or any combination. As such, each of the following features that will be discussed as well as any of the features described above in relation to the first aspect may be, but are not required to be, used with any other feature or combination of features of the second aspect.

For instance, in an embodiment the velocity signal may be a first derivative of the displacement signal with respect to time and the acceleration signal may be a second derivative of the displacement signal with respect to time. The processing module may determine the occurrence of the leading edge of the instrument passing from the first medium to the second medium when the displacement signal is positive, the velocity signal is positive, and the acceleration signal is positive. In another application, the processing module may determine the occurrence of the leading edge of the instrument passing from the first medium to the second medium at an occurrence of the displacement signal exceeding a predetermined displacement signal value, the velocity signal exceeding a predetermined velocity signal value, and the acceleration signal each exceeding a predetermined acceleration signal value. Accordingly, a predetermined value for the displacement signal, the velocity signal, and the acceleration signal may be established prior to commencing the operation. In an embodiment, if and only if each of the predetermined values are exceeded by each of these signals may an occurrence be determined. The predetermined values for each of the displacement signal, the velocity signal, and acceleration signal may correspond to a particular operation. Furthermore, the predetermined values of the signals may be determined at least partially on other parameters such as the patient, data regarding the patient, the bone on which the operation to be performed, the identity of instrument, or other relevant parameters.

In an application, the displacement sensor may be a linear variable differential displacement transducer. In another application, the sensor may be an optical transducer. For instance, the optical transducer may be operative to determine the displacement value based on sensor markings disposed on the instrument that are sensed by the optical transducer. In yet another application, the sensor may be a laser displacement sensor.

The processing module may be operative to generate an alert upon the occurrence of the leading edge of the instrument passing from the first medium to the second medium. In this regard, upon detection of an occurrence of the leading edge of the instrument passing from a first medium to the second medium, the processing module may output an occurrence signal. In response to the occurrence signal, an alert may be generated. The alert may be perceivable by a user of the instrument. In one application the alert may be an auditory alert. In another application, the alert may include a change in speed of the instrument that is perceivable by the user. For instance, the alert may include stopping the supply of power to the instrument, thus arresting the instrument.

As described above, in an application the displacement sensor may be disposed in an instrument guide that is external to and separate from the instrument. The instrument guide may be disposed about at least a portion of the instrument. For example, the instrument guide may include a cylindrical opening through which the instrument passes. As described above, in response to determination of an occurrence, an alert may be generated. In an application, the alert may include a physical stop in the instrument guide engaging the instrument. In this regard, the physical stop may arrest or at a minimum slow the instrument in a manner that is perceivable by the user. Accordingly, the instrument guide may include a physical stop responsive to the occurrence (e.g., as an alert) to act on the instrument. The physical stop may include a clamping element responsive to the occurrence (e.g., an occurrence signal) to clampingly engage the instrument.

It may be appreciated that the instrument guide may be maintainably engageable against a peripheral portion about a portion of the medium through which the instrument is advanced. As such, the instrument guide may define a reference point relative to the peripheral portion of the medium in a direction along an axis of advancement of the instrument. For instance, the instrument guide may be manipulated by the user to maintain engagement of the instrument guide against the peripheral portion of the medium through which the instrument is advanced. Additionally or alternatively, the instrument guide may include features that are engageable with a plate, fixture, or other structure disposed adjacent to or fixed to the medium through which the instrument is advanced. For example, the instrument guide may be in threaded engagement with a fixture adjacent to the medium through which the instrument is to be advanced. In any regard, the instrument guide may be maintained stationary relative to the medium through which the instrument is to be advanced to assist in defining a reference point from which the movement of the instrument may be monitored by the sensor.

In an embodiment, the instrument measurement system may determine, with respect to a reference point, a depth of penetration of the leading edge of the instrument at the occurrence of the leading edge of the instrument passing from the first medium to the second medium. That is, at the occurrence signal, the value of the displacement sensor corresponding to the displacement of the leading edge of the instrument relative to the reference point may be output to the user to provide a depth measurement associated with the leading edge of the instrument relative to the reference point. As such, the output of the displacement value may alleviate or reduce the reliance on a depth gauge or other additional tools used to measure the depth of the instrument in the medium.

In an embodiment, the processing module may be operative to process occurrence signals to account for noise or other errors in the signal that may be generated. For example, in an embodiment the processing module may apply a filter such that an occurrence cannot occur within a predetermined amount of time subsequent to another occurrence. In turn, bounce or other noise-induced signal characteristics may be filtered from the signals by applying the filter such that an occurrence cannot occur within a predetermined amount of time subsequent to another occurrence. This may prevent multiple rapidly occurring occurrences from being detected if the instrument bounces or chatters at the interface of the first and second medium.

In accord with the foregoing description regarding the various applications in which the measurement system may be applied in the context of a bone having a plurality of layers, in an application the first medium may be cortical bone surrounded by the second medium (e.g., an ambient environment such as air or other tissue of the patient) and the first medium may enclose a third medium having a third density. In this application, the system may further include a mode selector and the processing module may be further configured to operate in a mode selected from the group of modes consisting of: a first mode wherein the instrument travels along a unicortical path; and a second mode wherein the instrument travels along a bicortical path. When in the first mode, the occurrence of the leading edge of the instrument passing from the first medium to the second medium may be a first occurrence during an operation. That is, when applied in a unicortical operation, the instrument may pass through a single portion of the bone such that the first occurrence of the leading edge of the instrument passing from the first medium to the second medium may result in the occurrence signal being generated in accord with the unicortical operation described above. When in the second mode, the occurrence of the leading edge of the instrument passing from the first medium to the second medium may be a second occurrence. A first occurrence in the second mode may be when the instrument passes from the first medium to the third medium. In turn, the second occurrence may be when the instrument passes from the first medium (e.g., the hard outer cortex of the bone) to the second medium (e.g., and ambient environment such as air or surrounding tissue).

A third aspect includes a method for determining an occurrence of when a leading edge of an instrument passes from a first medium to a second medium contiguous with the first medium, where the first medium has a first density and the second medium has a second density. The method includes outputting a signal corresponding to movement of the leading edge of the instrument relative to a reference point. The method further includes generating a displacement signal, a velocity signal and an acceleration signal based on the signal corresponding to the movement of the leading edge of the instrument relative to the reference point. The method also includes determining an occurrence of the leading edge of the drill bit passing from the first medium to the second medium based only on the displacement signal, the velocity signal, and the acceleration signal.

A number of feature refinements and additional features are applicable to the third aspect. These feature refinements and additional features may be used individually or any combination. As such, each of the following features that will be discussed as well as any of the features described above in relation to the first or second aspects may be, but are not required to be, used with any other feature or combination of features of the third aspect.

For instance, in an application the signal corresponding to the movement of the leading edge of the instrument relative to the reference point may include the displacement signal, and the generating may include calculating the velocity signal as a first derivative with respect to time of the displacement signal and calculating the acceleration signal as a second derivative with respect to time of the displacement signal. The occurrence of the leading edge of the instrument passing from the first medium to the second medium may be determined when the displacement signal is positive, the velocity signal is positive, and the acceleration signal is positive. As described above, in another application, the determining may include determining the occurrence of the leading edge of the drill bit passing from the first medium to the second medium at an occurrence of the displacement signal exceeding a predetermined displacement signal value, the velocity signal exceeding a predetermined velocity signal value, and the acceleration signal each exceeding a predetermined acceleration signal value.

In an application, the method may also include generating an alert upon the occurrence of the leading edge of the instrument passing from the first medium to the second medium. The alert may be perceivable by a user of the instrument. For example, the alert may be an auditory alert. Additionally or alternatively, the generating the alert may include changing an angular velocity of the instrument in case of a rotating instrument, or changing the speed of oscillation of an oscillating instrument such as a saw. Generating the alert may also include stopping rotation of the instrument in the case of a rotating instrument or ceasing oscillation of an oscillating instrument. The outputting may be in response to the instrument passing through an instrument guide disposed about at least a portion of the instrument. The stopping may include applying a clamping force on the instrument by the instrument guide.

In an application, the method may further include measuring, with respect to a reference point, a depth of penetration of the leading edge of the instrument at the occurrence of the leading edge of the instrument passing from the first medium to the second medium. Additionally, the method include outputting an indication of the depth of penetration of the leading edge of the instrument at the occurrence of the leading edge of the instrument passing from the first medium to the second medium. Also as described above, the method may include applying a filter such that the occurrence cannot occur within a predetermined amount of time subsequent to another occurrence.

While the foregoing provides a summary of the disclosure presented herein, it may be understood that additional variations or combinations of features may be provided. Accordingly, the foregoing discussion and the discussion to follow is not intended to limit the scope of the present application. For example, each of the foregoing features, feature refinements, and additional features presented with respect to the first, second, and third aspects may be viewed as elemental features that may be used in any particular combination of feature elements described above. In this regard, the subject matter the present application is not limited solely to the specific embodiments described above or below in the detailed description, but may include further additional combinations of elements described herein.

BRIEF DESCRIPTION OF THE FIGURES

FIG. 27 is an embodiment of a saw having a measurement system for use with a fixture.

FIG. 31A-33B depict various embodiments of an instrument guide.

DETAILED DESCRIPTION

Figure 1A:
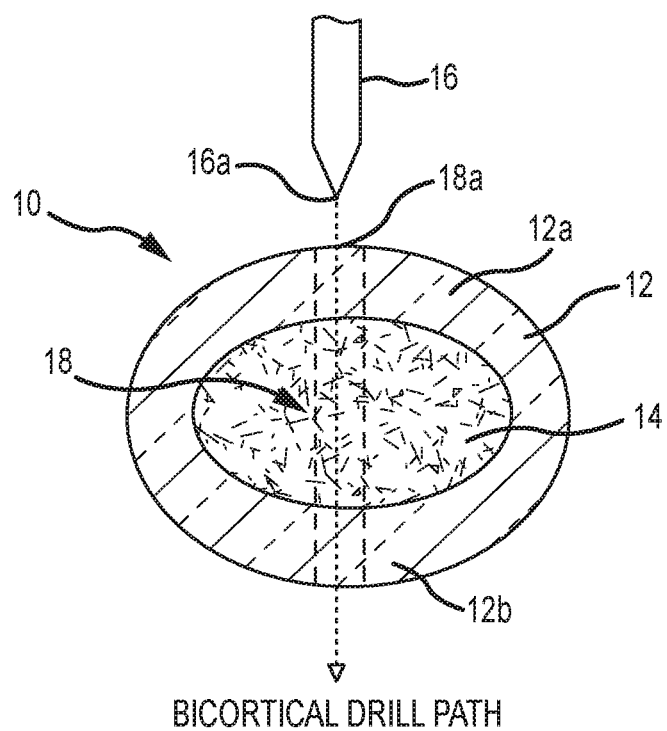
FIG. 1A is a sectional view of a bone illustrating a prior art method of using a drill to create a bicortical path through a cortical bone having multiple layers.

Certain terminology is used in the following description for convenience only and is not limiting. The words "right," "left", "lower" and "upper" designate directions in the drawings to which reference is made. The words "inwardly" and "outwardly" refer to directions toward and away from, respectively, the geometric center of the drill bit penetration measurement system and designated parts thereof. The terminology includes the words above specifically mentioned, derivatives thereof and words of similar import.

Additionally, as used in the claims and in the corresponding portion of the specification, the word "a" means "at least one". Further, unless otherwise defined the word "about" when used in conjunction with a numerical value means a range of values corresponding to the numerical value plus or minus ten percent of the numerical value. Still further, the word "or" has the meaning of a Boolean inclusive "Or". For example, the phrase "A or B" means "A" alone or "B" alone or both "A" and "B".

Figure 2:
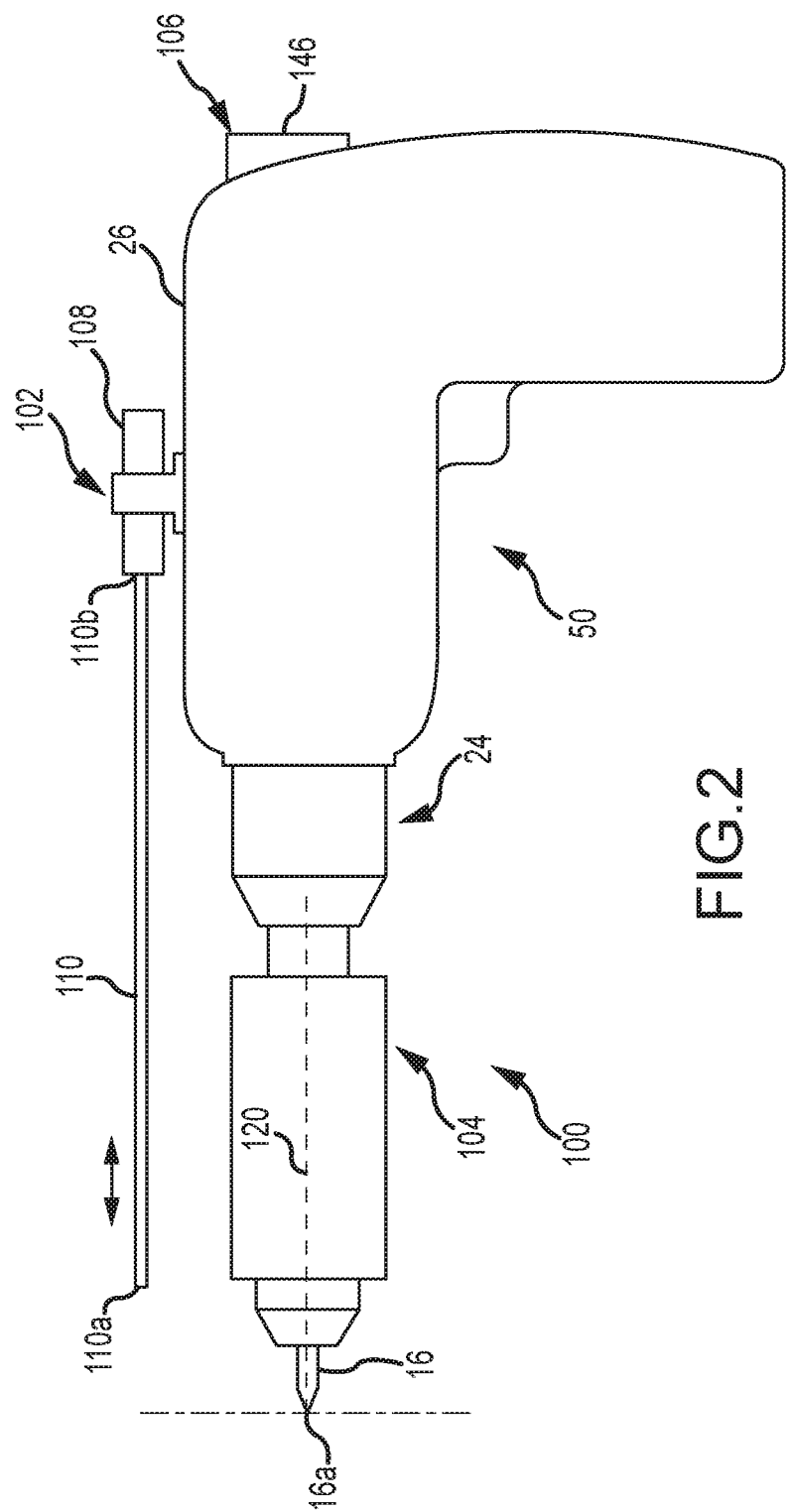
FIG. 2 is an elevation view of an embodiment of a measurement system used in conjunction with a drill.
Figure 3:
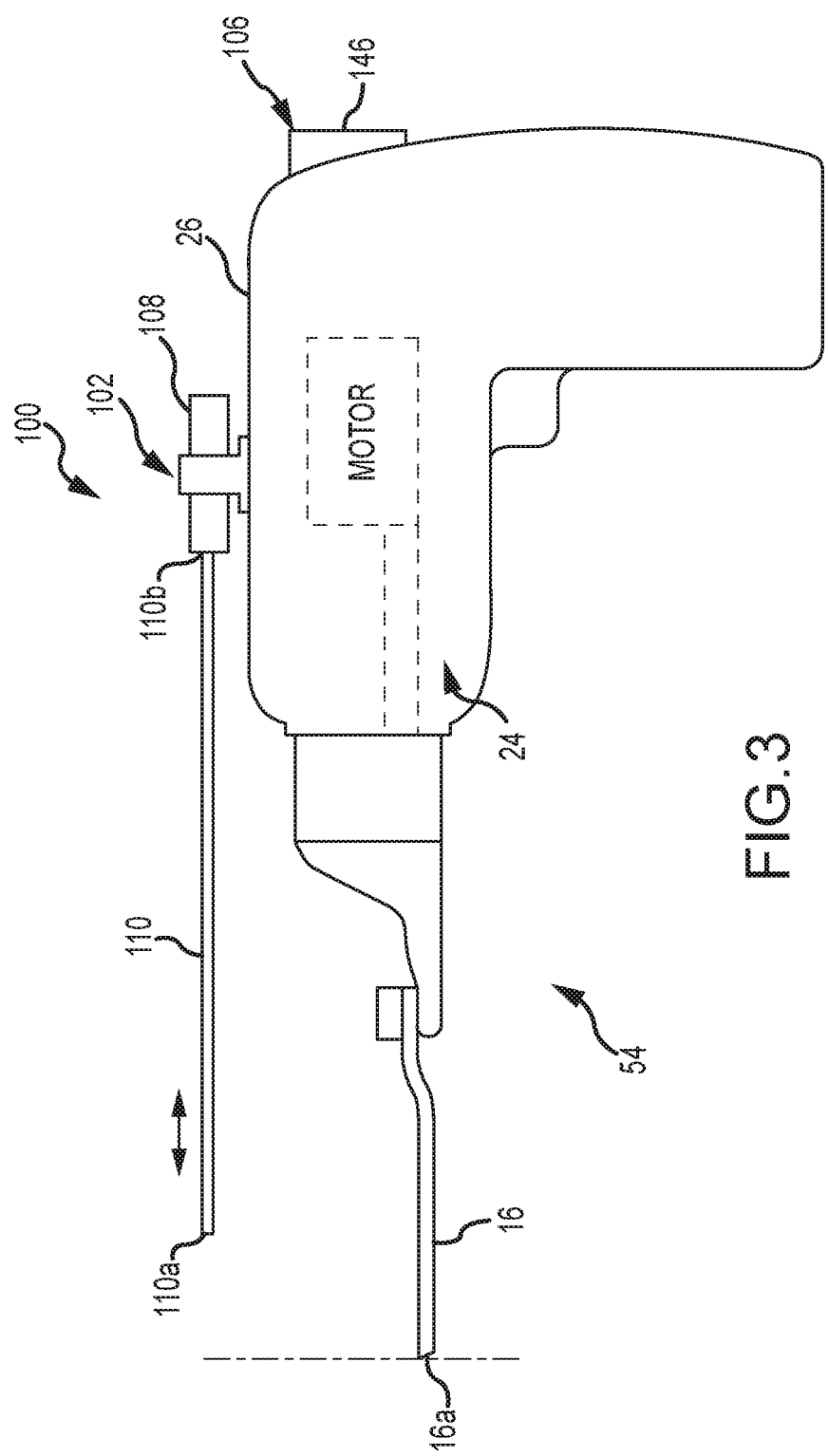
FIG. 3 is an elevation view of an embodiment of a measurement system used in conjunction with a saw.
Figure 4:
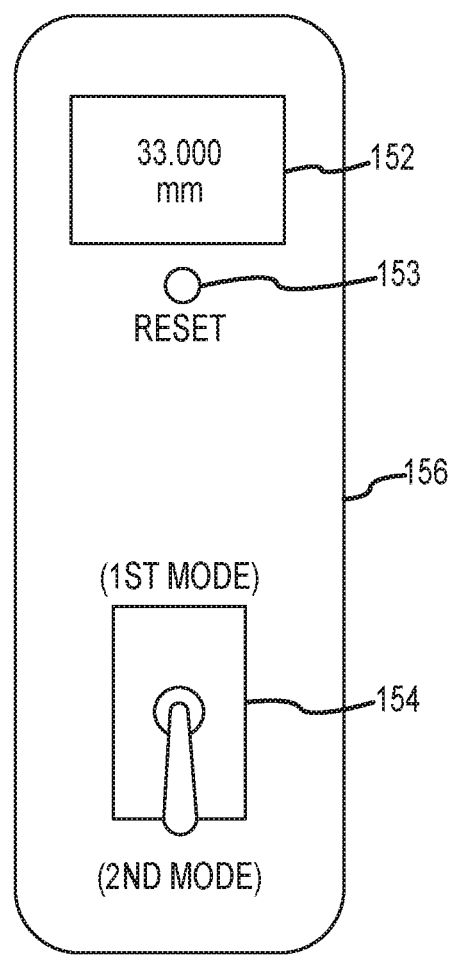
FIG. 4 is an elevation view of an embodiment of a control panel of a controller assembly.
Figure 5:
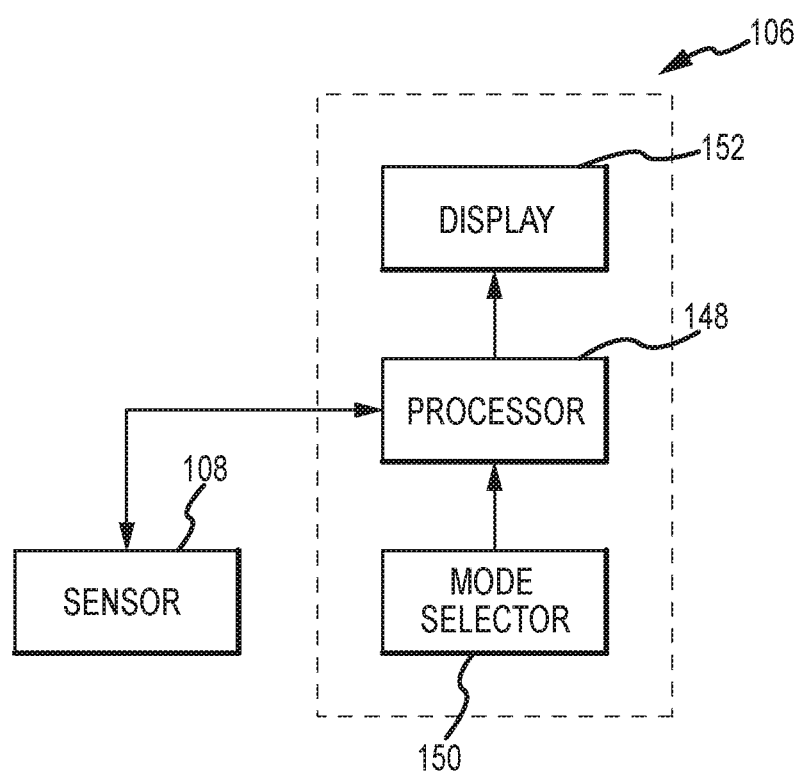
FIG. 5 is a schematic block diagram of a controller.

Referring to the drawings in detail, where like numerals indicate like elements throughout, there is shown in FIG. 2 an embodiment of a drill bit penetration measurement system generally designated 100 in accordance with the present invention. The measurement system 100 may facilitate determining an occurrence of the leading edge 16a of an instrument 16 passing from a first medium having a first density to a second medium adjacent the first medium and having a second density. FIG. 2 depicts the measurement system 100 employed in the context of a drill 50, wherein the instrument 16 comprises a drill bit. However, with further reference to FIG. 3, the system 100 may also be implemented in a context where the instrument 16 comprises a saw 54 having a saw blade. As such, it may be appreciated that the instrument 16 may be any appropriate implement used in a powered instrument. Thus, while examples may be discussed herein related to the context of a drill 52 or a saw 54, such examples are not intended to be limiting and the discussion presented herein may be generally applicable to any powered instrument where a leading edge 16a of the instrument 16 passes from a first medium to a second medium. The first medium may be a hard outer cortex of a bone and the second medium may be a soft medullary layer of a bone. Additionally or alternatively, the first layer may be a soft medullary layer of a bone and the second layer may be a hard outer cortex of a bone. Further still, the first medium may be a hard outer cortex of a bone and the second medium may be a medium surrounding the bone (e.g., air or soft tissue). In this regard, in various aspects or applications of the present invention, the first and second medium may be respectively chosen from materials comprising a hard outer cortex of a bone, a soft medullary layer of a bone, a medium exterior to the bone, or some other relevant structure relative to the bone.

Continuing with a discussion using the drill 50 as an example, the drill bit 16 is rotatably driven by a drive 24 in a drill housing 26 of any typical well known surgical drill. In this regard and as may be appreciated below, a measurement system 100 may be provided with an existing powered instrument such as a surgical drill 50, a surgical saw 54, or other surgical instrument (e.g., as a retrofit to the existing instrument). In further embodiments described in greater detail below, a measurement system 400 may be provided that is at least partially integrated into a drill or other appropriate powered instrument.

Figure 1B:
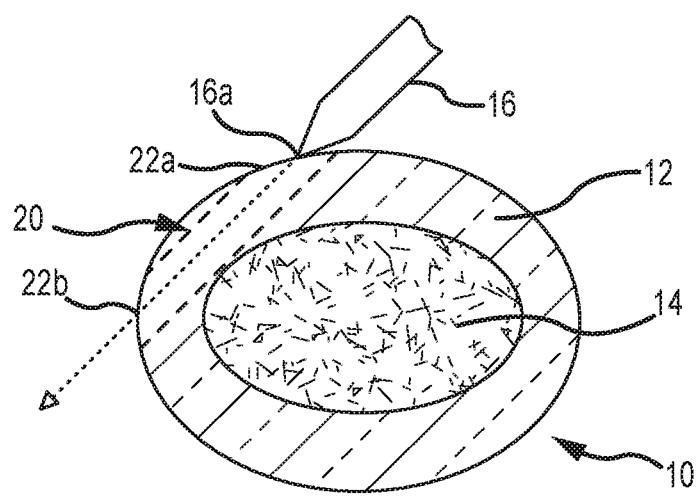
FIG. 1B is a sectional view of a bone illustrating a prior art method of using a drill to create a unicortical drill path through the outer layer of a cortical bone.
Figure 1C:
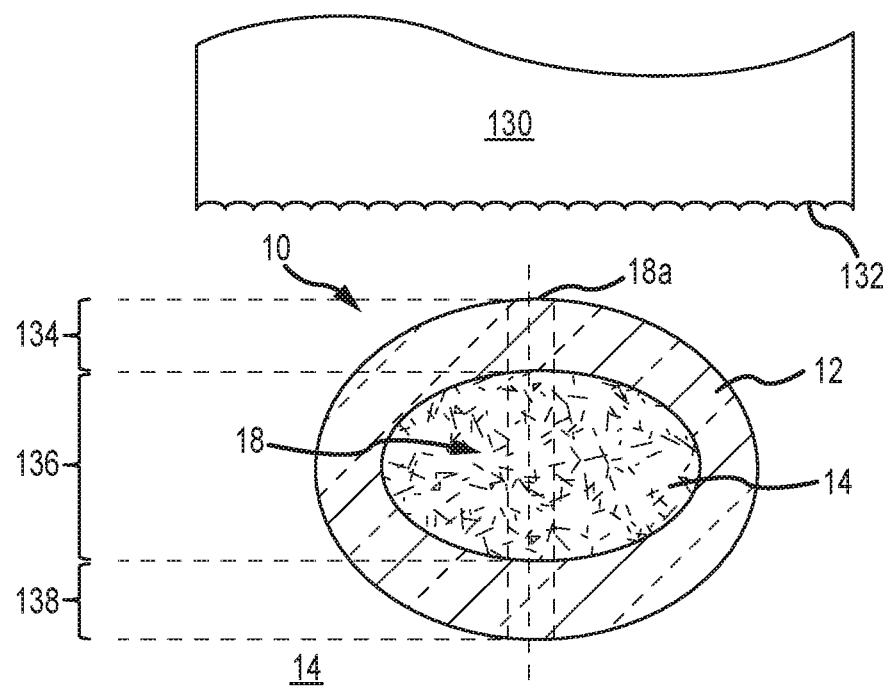
FIG. 1C is a sectional view of a bone illustrating a prior art method of using a saw to cut through a cortical bone having multiple layers.

As discussed above in relation to FIGS. 1A-1C, the first and second media may be a hard outer cortex 12 and a medium such as air or other structure (not shown) surrounding the outer surface of the cortical bone 10. Furthermore, the path through which the leading edge 16a is passed may either be a bicortical path 18 or a unicortical path 20 through the cortical bone 10. (See FIGS. 1A-1C). However, the first and second media may also, in some embodiments, be the hard outer cortex 12 and the soft inner medullary layer 14 of the cortical bone 10 or any adjacent media of different density without departing from the scope of the present disclosure.

In some embodiments, a reference point may be established from which the displacement of the leading edge 16a is measured. In this regard, the reference point may be a fixed point relative to which the displacement of the leading edge 16a of the drill bit 16 is measured and may correspond to an initial position of the measurement system 100 as further discussed below.

The measurement system 100 may include a displacement measurement assembly 102 and a controller assembly 106. The displacement measurement assembly 102 is connected to the housing 26. The connection can be made by a variety of well known mounting methods such as a mount that clamps to the displacement measurement assembly 102 and is attached to the housing 26 by one or more threaded fasteners. Alternative methods such as welding or adhesive bonding could also be used. The displacement measurement assembly 102 outputs a displacement signal 108s representative of a displacement, with respect to the reference point, of the leading edge 16a of the instrument 16 relative to the medium through which the leading edge 16a of the instrument 16 is passed. The displacement measurement assembly 102 may have an extension 110 that is displaceable along a longitudinal axis. The extension 110 has a distal end 110a that can be placed in registry with the reference point when the leading edge 16a of the instrument 16 is positioned at the entry point, such as the entry point 18a of the bicortical bore 18 shown in FIGS. 1A and 1C or the entry point 22a of the unicortical bore 20 shown in FIG. 1B, and maintained in registry with the reference point throughout the process. The reference point can be any anatomical structure proximal to the location where the instrument 16 interfaces with the medium. The extension 110 has a proximal end 110b that is attached to the displacement sensor 102. The sensor 102 may be any appropriate absolute or relative displacement sensor capable of outputting a displacement signal 108s.

In this regard, the displacement sensor may comprise a linear encoder capable of providing an absolute or relative displacement measure. Examples of appropriate displacement sensors 102 may include, but are not limited to, a linear variable differential displacement transducer ("LVDT"), an optical displacement sensor, a laser displacement sensor, an ultrasonic sensor, a magnetic displacement sensor, a Hall effect sensor, etc. In this regard, it may be appreciated that the sensors described herein utilize contactable engagement with the medium to be drilled to determine depth measurement, however, non-contacting depth measurement sensors may also be used such as laser sensors, proximity sensors, or the like.

Figure 28:
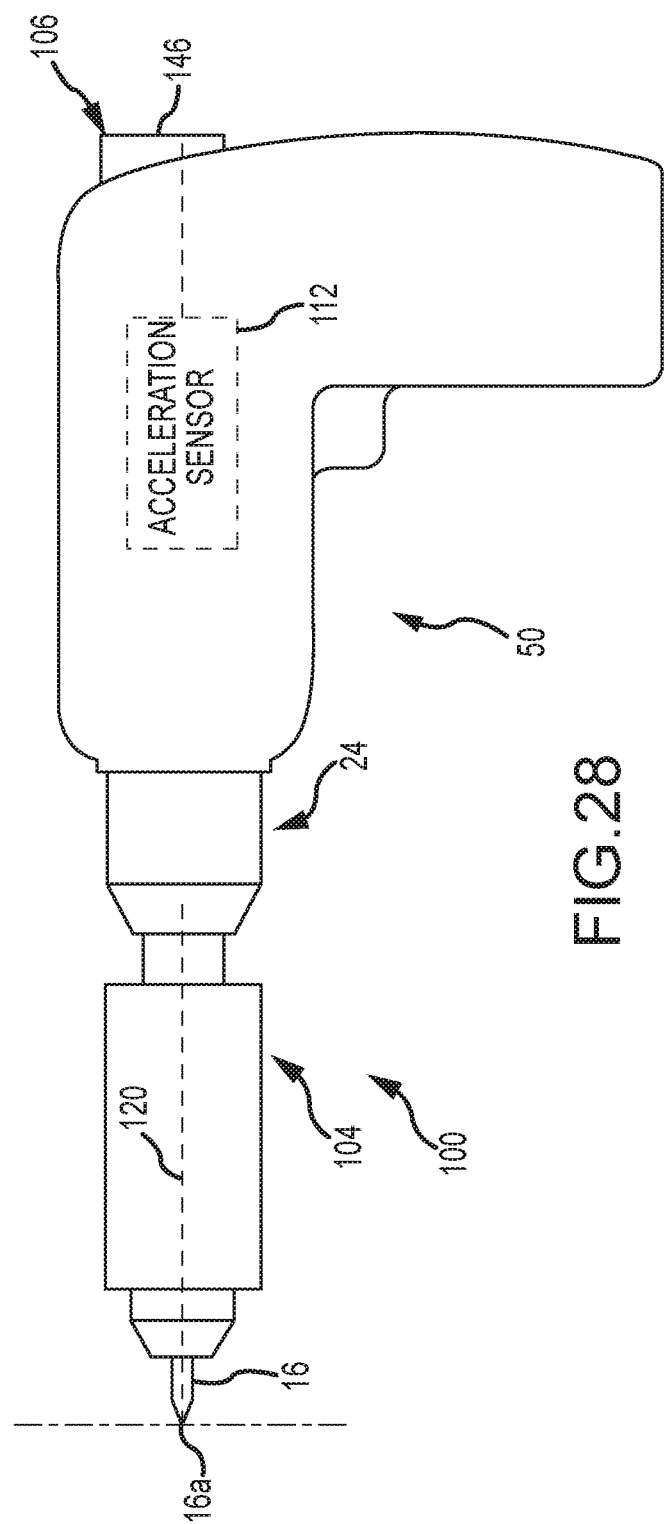
FIG. 28 is an embodiment of an instrument that included an acceleration sensor.

In another embodiment shown in FIG. 28, the drill 50 may include an acceleration sensor 112 or accelerometer and a controller assembly 106. The acceleration sensor 112 may be disposed within the drill housing 26 or may be provided external to the housing 26 (e.g., attached to an exterior of the housing or as a discrete, separate unit from the drill 50). In an embodiment, the acceleration sensor 112 may be a MEMS sensor capable of measuring an acceleration of the instrument 16 (e.g., including a leading edge 16a thereof). In any regard, the acceleration sensor 112 may be operative to measure an acceleration of a leading edge 16a of the instrument 16 relative to a medium through which the instrument 16 passes. In turn, velocity and/or displacement measures may be derived from the acceleration sensor 112 as will be described in greater detail below.

With continued reference to the embodiment of a drill 50 shown in FIG. 2, the drill 50 may include a chuck 104. The chuck 104 has an axis of rotation 120 and may be removably connected to the drive 24 for rotation thereby. In turn, the chuck 104 may correspondingly rotate the instrument 16.

Referring to FIGS. 2-9 and 28, the controller assembly 106 is in electrical communication with the displacement sensor 108 and/or acceleration sensor 112. In an embodiment, the controller assembly 106 may have a controller housing 146 integral with the drill housing 26. However, with further reference to FIGS. 18A and 18B, the controller assembly 106 may also be provided as a remote unit. The controller assembly 106 includes a processor 148 in electrical communication with the displacement sensor 108 and/or acceleration sensor 112 and with a mode selector 150 having a mode selector switch 154 and a display 152 having a reset button 153. The display 152, the reset button 154 and the mode selector switch 154 are mounted in a panel 156 of the controller housing 146. Alternatively, the display 152 or the reset button 153 or the mode selector 154 or any combination thereof could be separately housed in a remote control unit that communicates with the displacement sensor 108 by a wired and/or wireless link. Alternatively and as discussed above, the controller 106 may be housed internally to the instrument. The display 152 may indicate the measured displacement of the leading edge 16a of the instrument 16 and/or other information to the user. The display 152 is controlled by the processor 148. The display 152 may continuously indicate the changing displacement of the leading edge 16a of the instrument 16 and may also indicate the displacement of the leading edge 16a of the instrument 16 when the leading edge 16a passes from one medium to another.

Figure 18B:
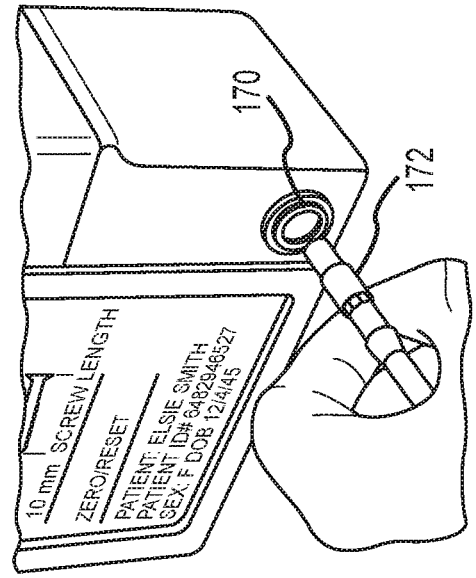
FIGS. 18A and 18B depict an embodiment of a controller for use in operation of a drill having a drill bit penetration measurement system.
Figure 18A:
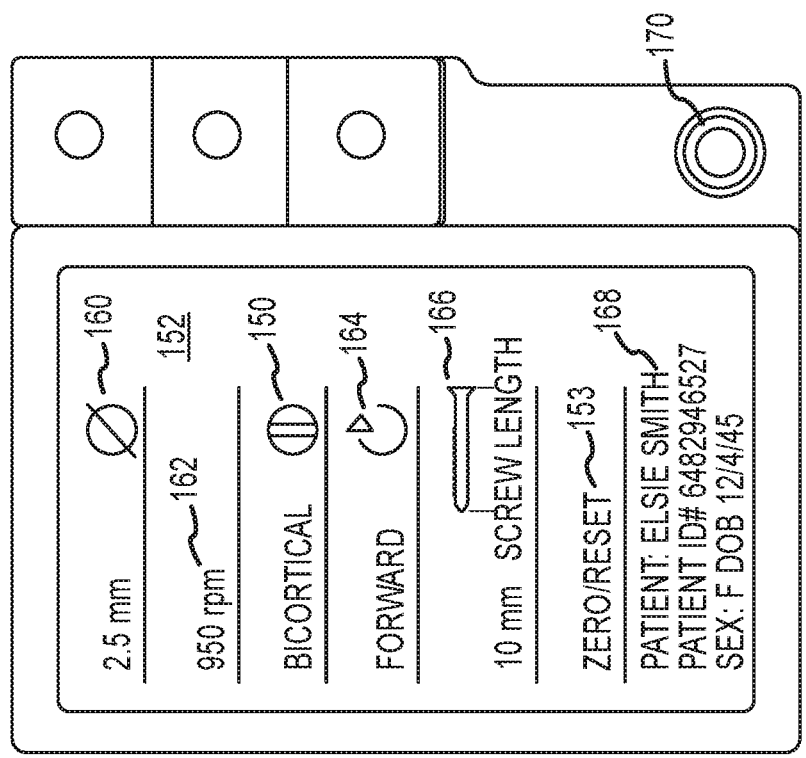

In an embodiment shown in FIGS. 18A and 18B, the controller assembly 106 may be a remote unit in operative communication with the displacement sensor 108. The display 152 may be a touch sensitive display (e.g., a resistive or capacitive type touch screen display). The display 152 may, in the context of use with a surgical drill, include an indication of a bore diameter 160, the drill speed 162, a drill direction 164, and a screw size indicator 166. In other contexts (e.g., when used with a bone saw or the like), other relevant parameters may be displayed including, for example, a displacement of a leading edge 16a relative to a medium through which the leading edge 16a is advanced. In any regard, the display 152 may also include patient information 168. The controller unit 106 may include a port 170 for engagement of a wired plug connection 172 for establishing operative communication with the displacement sensor 108. In this regard, the displacement sensor 108 and/or acceleration sensor 112 (e.g., whether integrated or separate from an instrument) may be connected to the controller assembly 106 to supply power to the sensor 108 and communicate data between the sensor 108 and the controller assembly 106.

The processor 148 may further be operative to execute one or more modules for performing functionality described herein. For example, the processor 148 may execute processing module, calculation module, an alert module, or other appropriate module for executing functionality described herein. In this regard, the processor 148 may be a general purpose microprocessor in operative indication with the memory that stores non-transitory machine-readable data accessible by the processor 148 to configure the processor 148 for execution of functionality described herein. Additionally or alternatively, the processor 148 may comprise application-specific integrated circuit (ASIC), a programmable field gate array, or other appropriate processor known in the art.

The processor 148 is configured to operate in a first mode for measurement of a unicortical path. In the first mode the processor 148 is configured to output an occurrence signal 148s representative of an occurrence of the leading edge 16a passing from the first medium to the second medium. In an embodiment, the occurrence signal 148s may be based solely on the displacement signal 108s, transforms of the displacement signal 108s, and/or mathematical outputs derived from the displacement signal 108s. That is, the occurrence signal 148s may be solely generated based on a measured signal from a single sensor. In a first embodiment, the single sensor may be the displacement sensor 108 that measures a displacement signal 108s. A velocity signal 108v and an acceleration signal 108a may be derived from the directly measured displacement signal 108s. In another embodiment, the single sensor may be the acceleration sensor 112 that measures an acceleration signal 108a. A velocity signal 108v and a displacement signal 108s may be derived from the directly measured acceleration signal 108a. In a further embodiment, a displacement sensor 108 and an acceleration sensor 112 may be provided in conjunction in the absence of a force sensor as has traditionally be used to determine an occurrence of a leading edge 16a of an instrument 16 passing from a first medium to a second medium.

Preferably, the occurrence signal 148s is output upon a first occurrence (in the case of a unicortical path) of the displacement signal 108s being greater than zero, the velocity signal 108v being greater than zero, and an acceleration signal 108a being greater than zero. In other words, a positive displacement, a positive velocity, and a positive acceleration of the instrument 16 occurring concurrently may trigger the first occurrence of the occurrence signal 148s. At the time of the first occurrence, the occurrence signal 148s may correspond to the length of the unicortical path or may be used to determine the occurrence of the leading edge 16A of the instrument passing into the medullary layer 14.

The processor 148 may also be configured to operate in a second mode for penetration measurement in a bicortical path and the mode selector 150 and mode selector switch 154 are for selecting between the first and second modes. The second mode of operation may correspond to the case where the first medium is the cortical bone 12 surrounded by a second medium, such as the air or tissue surrounding the outer surface of the cortical bone 12, and the first medium encloses a third medium, such as the soft medullary layer 14, having a third density. In the second mode, the processor 148 is configured to output the occurrence signal 148s in response to a second occurrence of the displacement signal 108s being greater than zero, the velocity signal 108v, and the acceleration signal 108a being greater than zero, and corresponds to the length of the bicortical path. Accordingly, the occurrence signal 148s is output after the second time the instrument 16 experiences concurrent positive displacement, positive velocity, and positive acceleration at the leading edge 16a of the instrument 16.

As may be appreciated from the foregoing, the controller 106 may be operative to output an occurrence signal 148 based on a displacement signal 108s, a velocity signal 108v, and an acceleration signal 108a. These signals may be derived by either of a displacement sensor 108 or an acceleration sensor 112. For instance, the displacement sensor 108 may directly measure the displacement signal 108s. The velocity signal 108v may be a first time derivative of the displacement signal 108s and the acceleration signal 108a may be a second time derivative of the displacement signal 108s. In the case of the acceleration sensor 112, the acceleration signal 108a may be directly measured by the acceleration sensor 112. The velocity signal 108v may be a first integral with respect to time of the acceleration signal 108a and the displacement signal 108s may be a second integral with respect to time of the acceleration signal 108a. As such, the discussion presented herein regarding determining an occurrence of the leading edge 16a of an instrument 16 passing from a first medium to a second medium based on a displacement signal 108s, a velocity signal 108v, and an acceleration signal 108a may the same regardless of how the displacement signal 108s, the velocity signal 108v, and the acceleration signal 108a are derived, so long as the respective signals are derived from a single sensor only.

Figure 6:
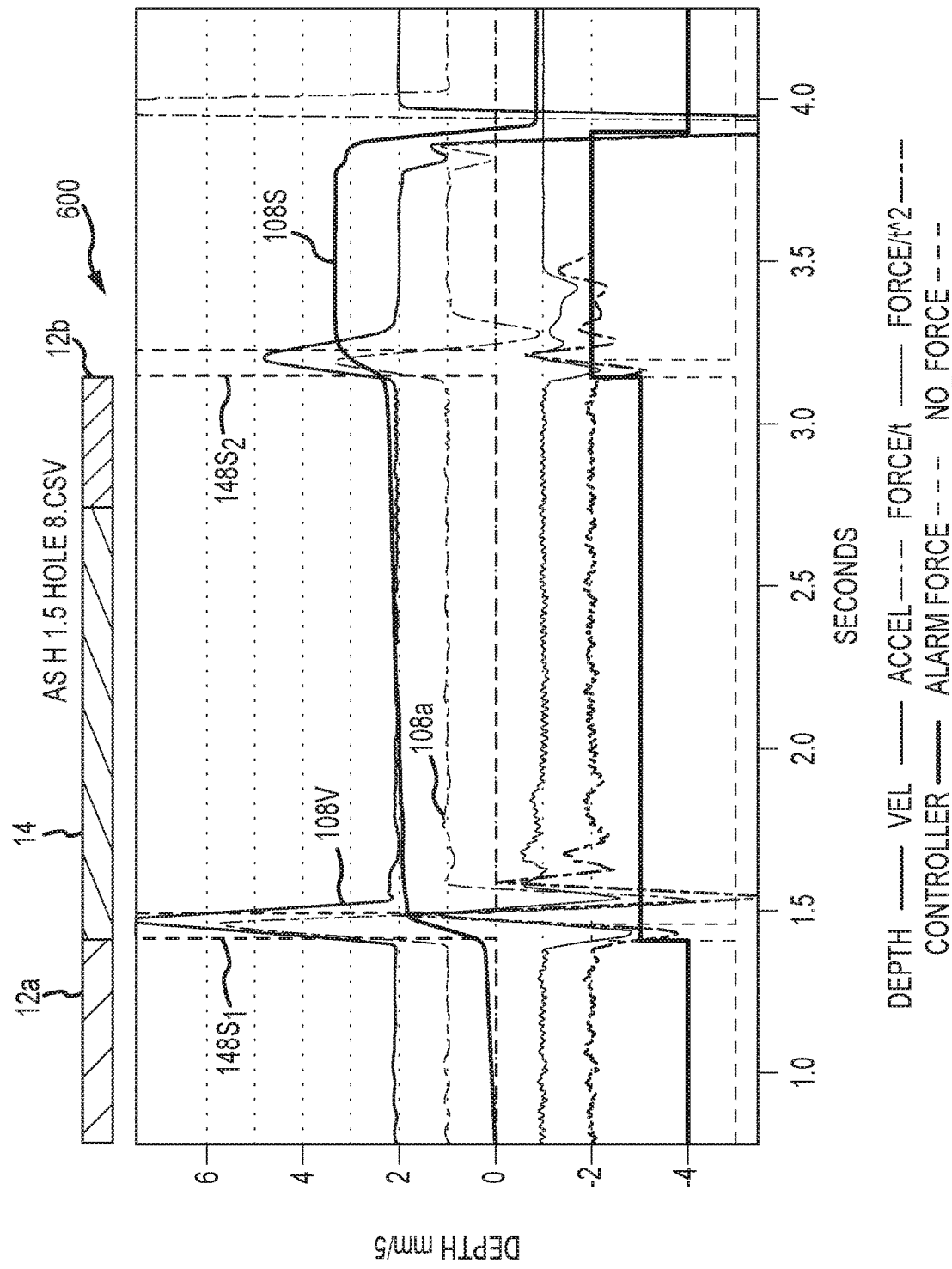
FIG. 6 is a graphical representation of an embodiment of a displacement sensor signal as used according to the present disclosure.

For example, with further reference to FIG. 6, a graphical depiction of the signals derived from a sensor during a bicortical operation using an instrument 16 shown. Above the graph in FIG. 6 is a representation 600 of the bicortical path that is presented in relation to the signals. That is, the representation 600 includes a first portion of a hard outer cortex 12a, a soft medullary layer 14, and a second portion of hard outer cortex 12b. These portions are aligned relative to the displacement signal 108s to assist in understanding the position of the instrument 16 relative to the anatomical structures during generation of the signals presented.

The displacement signal 108s (e.g., as measured by the displacement sensor 108 or derived from the acceleration sensor 112) is shown. The velocity signal 108v may be generated as discussed above. Additionally, the acceleration signal 108a is shown (e.g., as measured by the acceleration signal 112 or derived from the displacement senor 108 as discussed above). The displacement signal 108s, the velocity signal 108v, and the acceleration signal 108a may be provided based on a single sensor.

In this regard, the processor 148 may monitor the displacement signal 108s, the velocity signal 108v, and the acceleration signal 108a. Upon an occurrence of each of these signals being positive, an occurrence signal 148s may be generated. As can be appreciated, at the interface between the first portion of hard outer cortex 12a and the medullary layer 14, the displacement signal 108s, velocity signal 108v, and acceleration signal 108a all correspond to positive values. This positive value of displacement, velocity, and acceleration may correspond to the instrument 16 passing from the first portion of hard outer cortex 12a to the medullary layer 14. Accordingly, a first occurrence signal $148s_1$ may be output. Furthermore, a second occurrence of the occurrence signal $148s_2$ may occur as the instrument 16 passes from the second portion of the hard outer cortex 12b to the surrounding medium. This second occurrence $148s_2$ may occur where the displacement signal 108s, velocity signal 108v, acceleration signal 108a are all positive.

As may be appreciated, to overcome noise present in each of the signals, a number of signal processing approaches may be taken. For example, the positive values of the displacement signal 108s, the velocity signal 108v, and acceleration signal 108a may each exceed corresponding respective predetermined thresholds prior to output of an occurrence signal 148s. In this regard, noise that may be present in the measured and/or calculated signals may be filtered such that a predetermined value of each of the appropriate signals must exceed the predetermined positive value to trigger the occurrence of an occurrence signal 148s. The respective predetermined positive value for each signal may be tuned to avoid false occurrence signal 148s, yet provide sufficient sensitivity to accurately determine occurrences of the instrument 16 passing from a first medium to a second. Furthermore, a bounce filter may be applied to the signals such that an occurrence of an occurrence signal 148s may not occur within a predetermined period following another occurrence of an occurrence signal 148s. That is, rapidly successive occurrence signals may be prevented that may be associated with the instrument 16 bouncing or incurring chatter as it passes through the interface between the first medium and the second medium.

Figure 7:
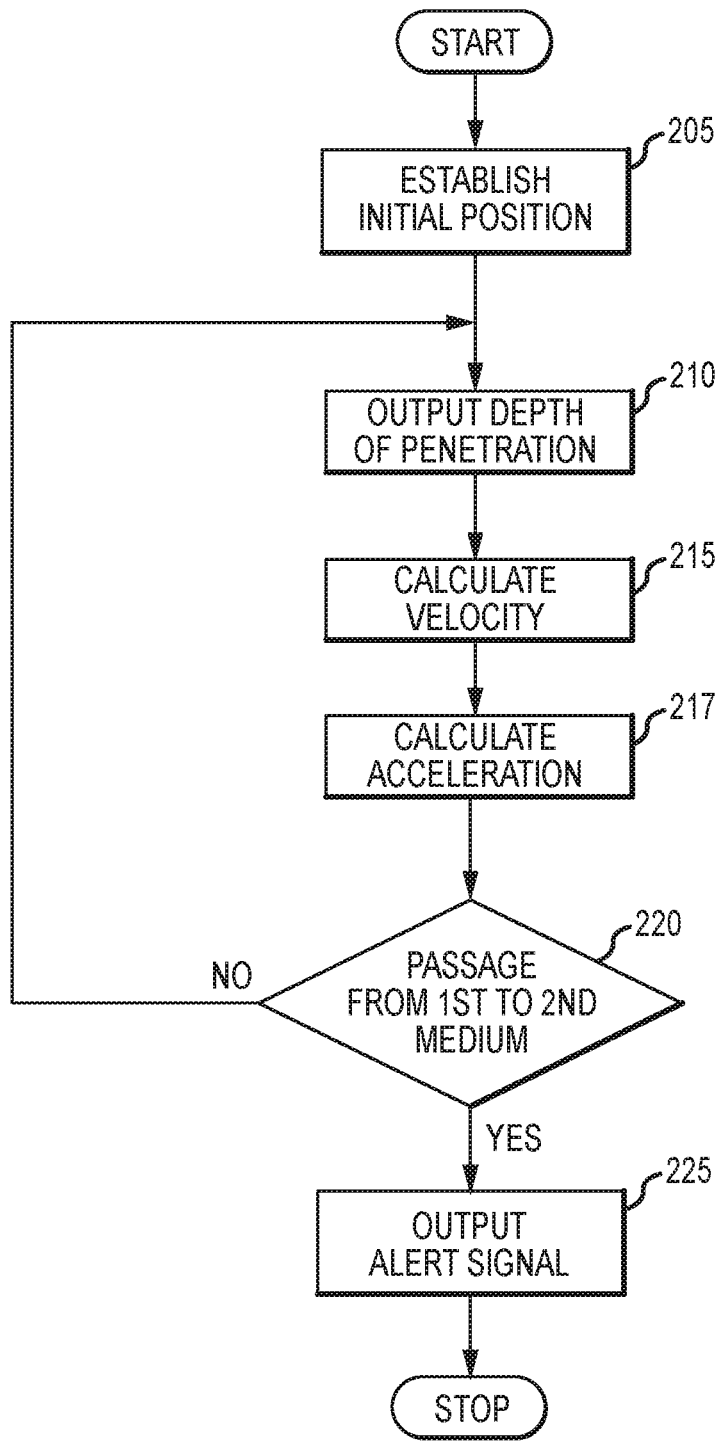
FIG. 7 is a flow diagram of an embodiment of a method for determining the depth of penetration of a drill bit.

Referring to FIG. 7, there is shown a block diagram of a first preferred method for determining, with respect to a reference point, the depth of penetration of the leading edge 16a of a instrument 16 along a path when the leading edge 16a of the instrument 16 transitions from a first medium having a first density, such as the hard outer cortex 12 of a cortical bone 10, to a second adjacent medium having a second density, such air or tissue surrounding the outer surface of the cortical bone 10.

An initial position of the leading edge 16a of the instrument 16 relative to the reference point may be established (Step 205). The initial position may be established by placing the leading edge 16a of the instrument 16 against the outer surface of the cortical bone to be drilled and by extending the distal end 10a of the extension 110 of the displacement measurement assembly 102 to the reference point, such as an anatomical structure proximal to the desired location of the instrument 16. With the leading edge 16a of the instrument 16 and the distal end 110a of the extension 110 in the above positions, the measured displacement of the instrument 16 is set to zero by pressing the reset button 153. Upon commencement of advancement of the leading edge 16a along a path through the cortical bone 10, a displacement signal 108s representing the depth of penetration of the leading edge 16a of the instrument 16 along the path is output (Step 210). A velocity signal 108v representing the velocity of the leading edge 16a of the instrument may be calculated (Step 215). The velocity signal 108v may be generated by taking the first time derivative of the displacement signal 108s. An acceleration signal 108a representing the acceleration of the leading edge of the drill bit may also be calculated (Step 217). The acceleration signal 108a may be generated by taking the second time derivative of the displacement signal 108s. An occurrence signal based on the displacement signal 108s, velocity signal 108v, and acceleration signal 108a may be generated when an occurrence of the leading edge 16a of the instrument 16 passes from the first medium to the second medium (Step 220). Preferably, the occurrence signal is output (Step 225) when the displacement signal 108s, velocity signal 108v, and acceleration signal 108a are all concurrently greater than zero as shown and described above in relation to FIG. 6.

Figure 8:
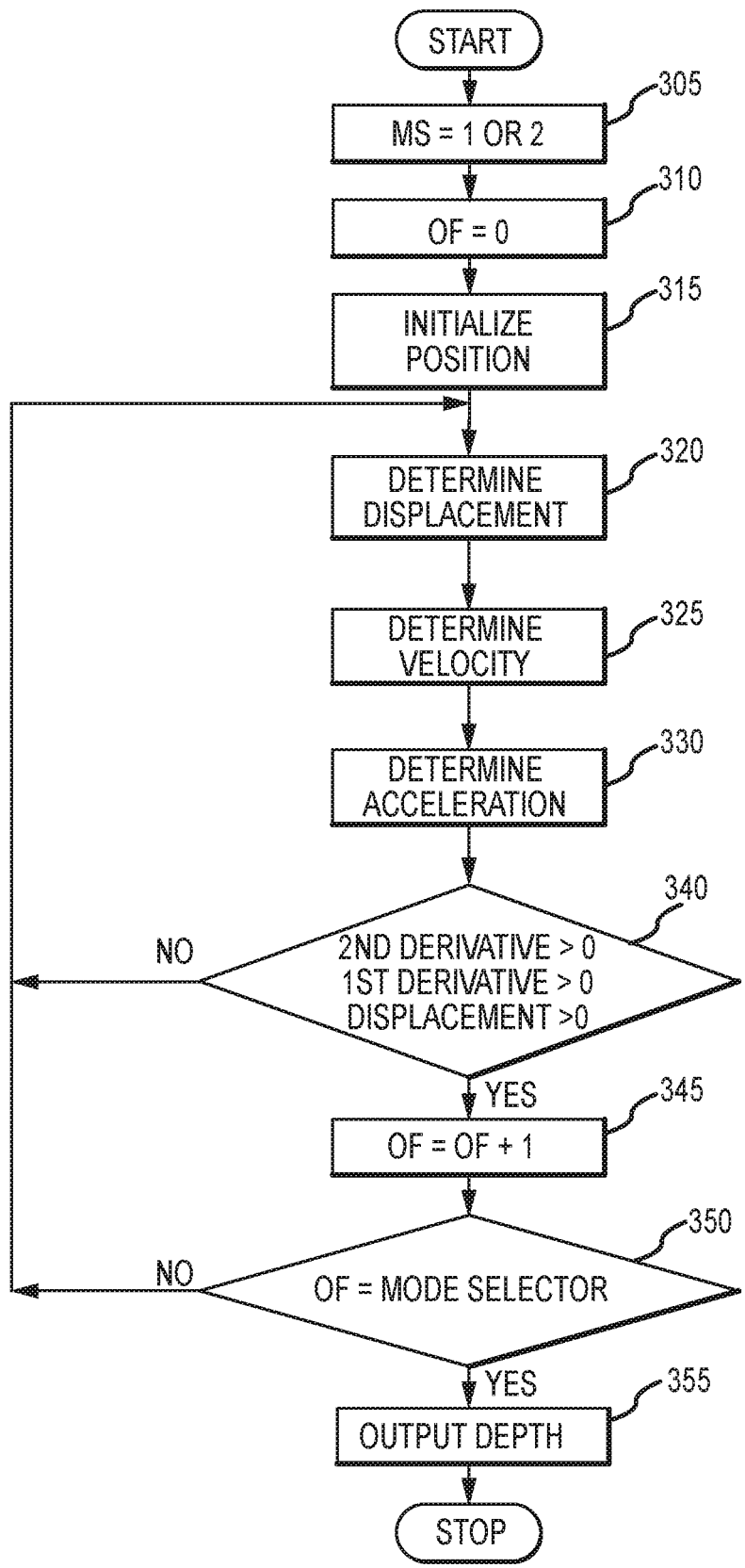
FIG. 8 is a flow diagram of an embodiment of a method for determining the depth of penetration of a drill bit.

Referring to FIG. 8, there is shown a block diagram of a second preferred method for determining, with respect to a reference point, the depth of a unicortical path or a bicortical path through a cortical bone 10. The mode selector switch 15 (MS) is set to the value "1" if a unicortical path 20 is being taken by the instrument 16 or set to the value "2" if a bicortical path 18 is being taken (Step 305). An occurrence flag (OF) is set to zero (Step 310). An initial position of the leading edge 16a of the instrument 16 relative to the reference point is established (Step 315), preferably in a manner similar to Step 205 discussed above. The displacement signal, the corresponding velocity signal 108v, and the corresponding acceleration signal 108a for the leading edge 16a of the instrument 16 are continuously determined, (Steps 320, 325, and 330, respectively). The occurrence flag is updated by adding one to its present value (Step 345) when an occurrence signal is generated as discussed above (Step 340), otherwise determination of the displacement signal 108s, velocity signal 108v, and acceleration signal 108a continues. The occurrence signal is output (Step 355) if the value of the occurrence flag is equal to the value of the mode selector (Step 350), otherwise determination of the displacement signal 108s, velocity signal 108v, and acceleration signal 108a continues.

Figure 9:
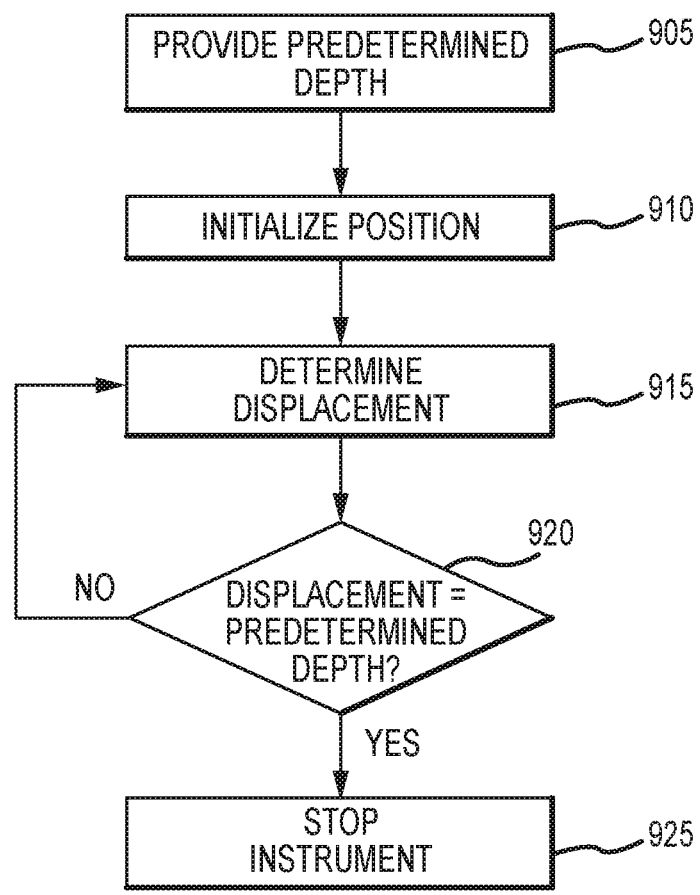
FIG. 9 is a flow diagram of an embodiment for control of an instrument.

Referring to FIG. 9, there is shown a block diagram of a second method for determining, with respect to a reference point, the length of a path taken by an instrument 16 with respect to a medium in which the instrument 16 is advanced. A predetermined depth to be reached by the instrument may be provided (Step 905). An initial position of the leading edge 16a of the instrument 16 relative to the reference point is established (Step 910), preferably in a manner similar to Step 205 discussed above. The displacement of the leading edge 16a of the instrument 16 is continuously determined (Step 915). The processor 148 may determine if the displacement of the leading edge 16a of the instrument 16 is equal to the predetermined depth provided (Step 920). If the depth does not equal the predetermined depth (i.e., is less than the predetermined depth), the operation may continue. Once the displacement equals the predetermined depth, the instrument may be stopped (Step 925).

Additionally or alternatively, in an embodiment the occurrence signal 148s may be at least partially based on additional parameters other than the displacement signal 108s, velocity signal 108v, and acceleration signal 108a. For instance, in at least some embodiments, the occurrence signal 148s may be at least partially based on a parameter associated with the instrument. For instance, the speed of the drive 24 powering the instrument 16, the resistance against the instrument 16 (e.g., as is measured by the load on a drive 24 powering the instrument 16), or another appropriate parameter regarding the instrument 16 may be utilized in outputting the occurrence signal 148s. Further still, parameters such as the length of the instrument 16, the bone on which the instrument is used, or other appropriate parameters may be utilized in determining the occurrence signal 148s.

Furthermore, the generation of the occurrence signal 148s may at least partially be customized based on the patient. In this regard, information regarding the patient may be provided to the controller assembly 106 and utilized by the processor 148 in determining the occurrence signal 148s. For instance, a patient's age, sex, and/or other demographic information may be provided. As may be appreciated, the demographic data of the patient may provide a correlation to expected bone density or other parameter regarding an expected property of the patient's anatomy based on the demographic data of the patient. In this regard, the demographic data may be used to correlate an expected parameter associated with the patient's anatomy (e.g., bone density) that may be used as a factor in generation of the occurrence signal 148s. In addition, direct measurement of an anatomical parameter (e.g., bone density) for a given patient may be provided directly to the controller assembly 106, thereby potentially eliminating the need to estimate the parameter based on demographic data.

Accordingly, the foregoing describes approaches to determining when the leading edge 16a of an instrument 16 passes first meeting the second medium. As such, when performing an operation relative to a bone 10, the measurement system 100 may be utilized to assist a surgeon in determining when the leading edge 16a of an instrument 16 is a particular portion of the bone structure 10. For example, in certain operations the leading edge 16a may be advanced through a first portion 12a of a hard outer cortex 12 such the leading edge 16a is arrested at the entry of the medullary layer 14. In other operations, the leading edge 16a may be advanced through the entire bone 10 such that the leading edge 16a is advanced through the entirety the bone out the second portion 12b of the hard outer cortex 12. Further still, in certain operations (e.g., placement of a transcutaneous pin) the leading edge 16a may be desirably advanced into the second portion 12b of hard outer cortex 12 for placement of the transcutaneous pin.

The components used to construct the present invention may consist of a variety of materials that are customarily used in the manufacture of surgical drills. One having ordinary skill in the art will readily appreciate the materials that most desirably may be used to construct the present invention. In an embodiment, however, the instrument drive mechanism, the displacement measurement assembly, and the structural elements of the controller assembly may be constructed of a combination of polymeric materials (e.g., high strength plastic), polymers, and metallic materials (e.g., stainless steel).

Furthermore, it may be appreciated that the spacing of the extension 110 of the displacement measurement assembly 102 from the instrument 16 may introduce the potential for errors in determining the displacement of the instrument 16 relative to the reference point. For instance, as the extension 110 may contact a structure that is offset from the contact point between the leading edge 16a of the instrument 16 and the medium through which the instrument is advanced. Accordingly, any movement between the structure contacted by the extension 110 and the medium may be falsely registered as relative movement of the instrument 16 with respect to the reference point. Furthermore, there may not be a rigid structure to contact adjacent to the medium to be drilled, leading to displacement of the structure contacted by the extension 110 (e.g., such as in the case where the extension 110 may contact soft tissue adjacent to the medium). Furthermore, the offset nature of the extension 110 relative to the contact between the instrument 16 and the medium to be drilled may lead to other complications such as having to expose a greater surface of the medium to be operated upon, which may adversely affect patient outcomes.

As such, a displacement sensing arm may be provided that extends from an instrument to more accurately provide a displacement measurement for a leading edge of the instrument. For example, such a displacement sensing arm may coordinate with a bushing member that is disposable relative to the instrument. In this regard, the bushing may move along the instrument in a direction corresponding to the axis of advancement of the instrument. Upon engagement of the bushing and the displacement sensing arm, the bushing and displacement sensing arm may undergo corresponding movement. As such, the bushing may be disposed in contact with the medium through which the instrument is to be advanced when the leading edge of the instrument is in contact with the medium. A reference point may be established when the bushing and leading edge of the drill bit are both in contact with the medium prior to operation of the powered instrument. As the bushing is located adjacent to (e.g., partially or fully surrounding the instrument), the bushing may facilitate contact with the medium at or very near the location where the instrument interfaces with the medium. In this regard, the reference point may be more accurately maintained as the bushing may contact a periphery of the entry of the path created in the medium by the instrument. That is, the bushing may remain in intimate contact with the medium to adjacent to the entry of the path created by the instrument. This may reduce false displacement readings attributable to the foregoing problems associated with an offset extension 110. Furthermore, the amount of contact the instrument has with the medium may be localized at the location where the instrument interfaces the medium, thus allowing for potentially less intrusion when performing operations.

Figure 10:
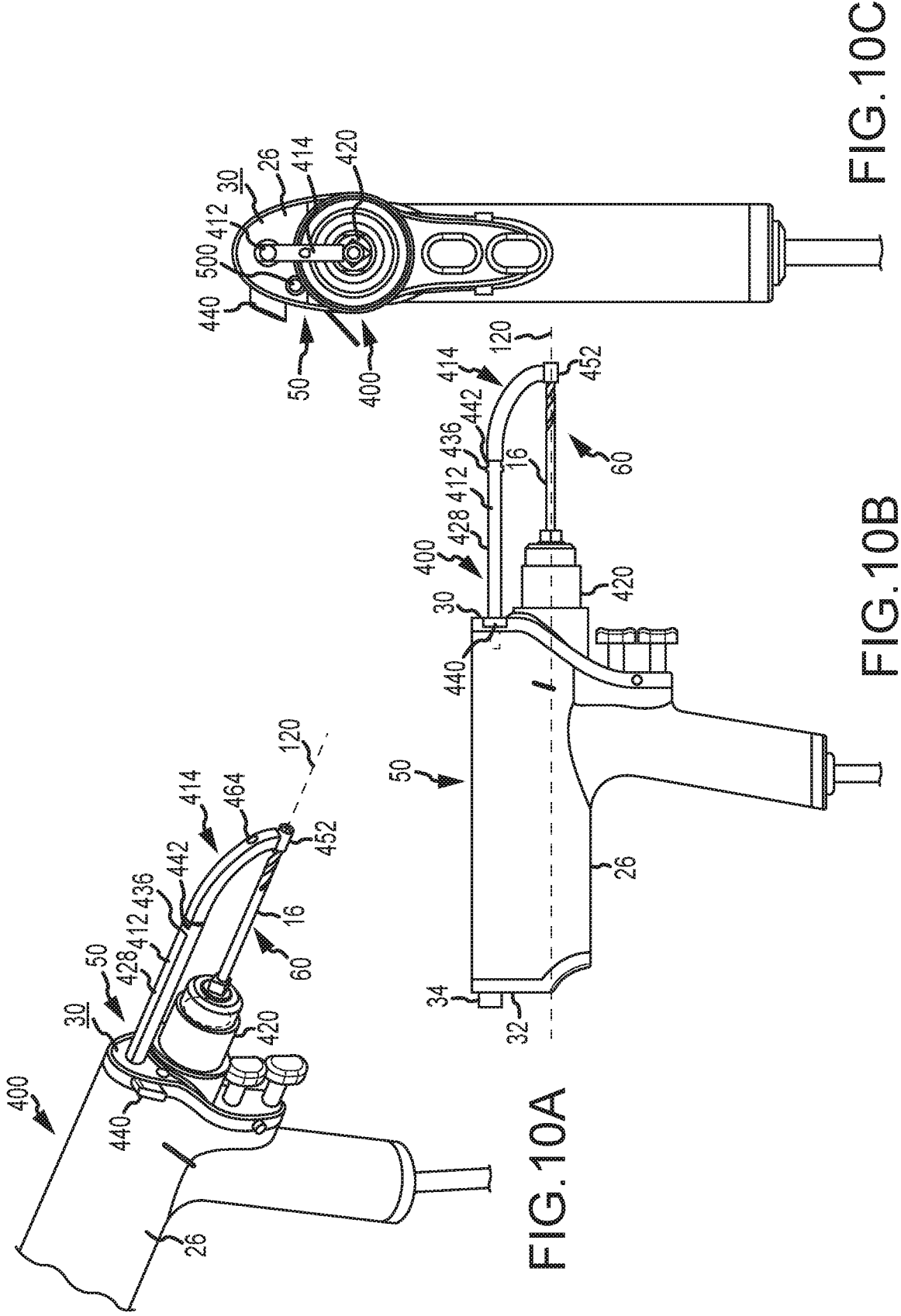
FIGS. 10A-10C are perspective, side, and front views, respectively, of an embodiment of a drill comprising a drill bit penetration measurement system.

For example, with additional reference to FIGS. 10A-10C, an embodiment of a drill 50 comprising an embodiment of a measurement system 400 is shown. However, as may be appreciated in regarding to the description provided below, other powered instruments such as saws, burrs, reamers, or the like may employ an embodiment of a measurement system 400 described in relation to FIGS. 10A-10C. The drill 50 may be adapted for use with a drill bit assembly 60 (shown in FIG. 12) that may include a bushing 452. The drill 50 may integrally comprise at least some components of the measurement system 400 to facilitate operation of the measurement system 400 in connection with the drill 50. For example, at least a portion of a displacement sensor 410 may be integrated into a housing 26 of the drill 50. In this regard, the displacement sensor 410 may include a depth sensing arm 412 that is specifically adapted for engagement with a bushing 452 of a drill bit assembly 60 that may be engaged by the chuck 420 of the drill 50.

In this regard, the depth sensing arm 412 may be used to establish a reference point from which displacement of the drill bit 16 may be measured as described above. In this regard, as follows herein, a general description of the features and operation of the drill 50 used in conjunction with the drill bit assembly 60 is provided.

Figure 11:
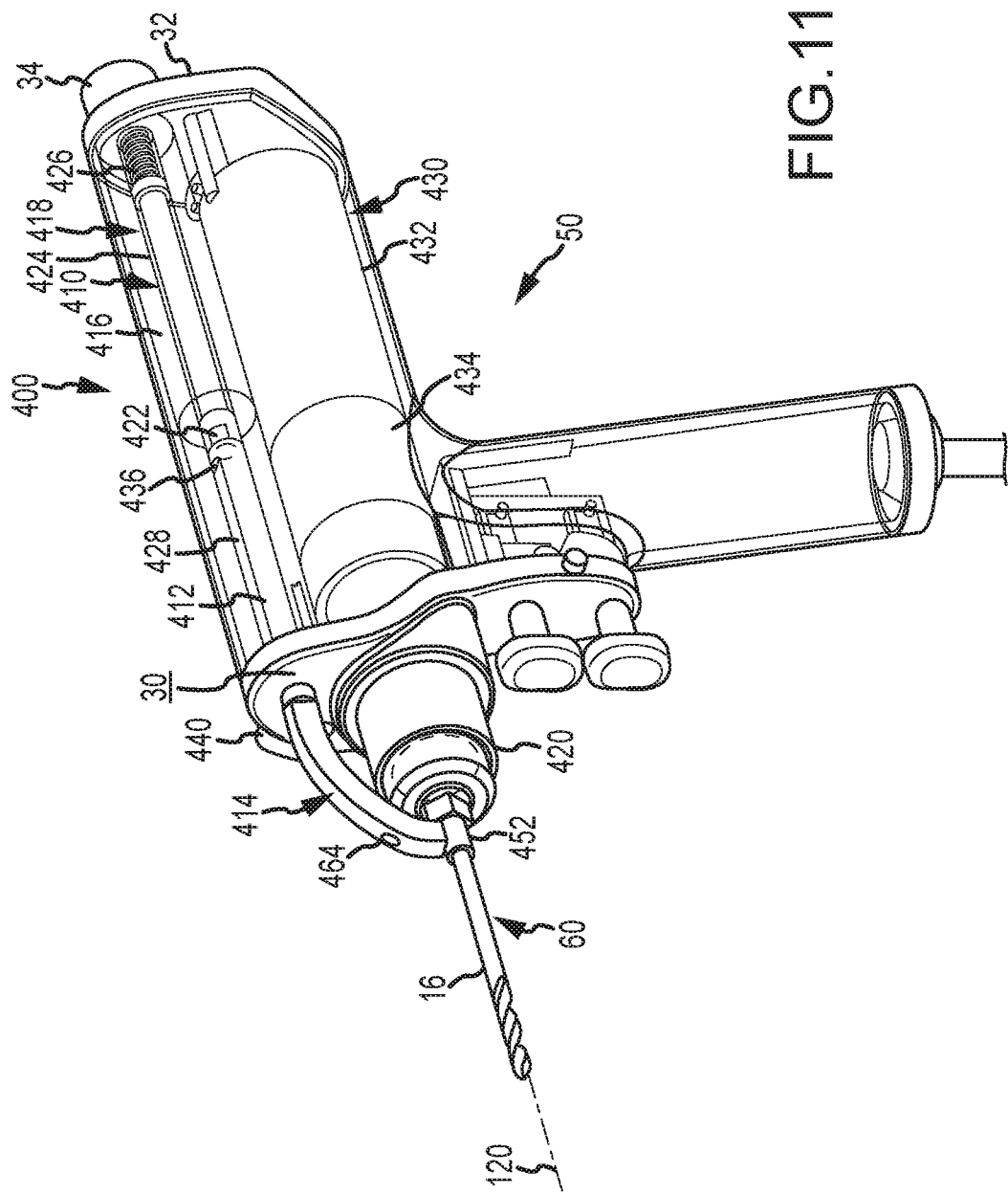
FIG. 11 is a perspective view in partial cutaway of an embodiment of a drill comprising a drill bit penetration measurement system.

As may be appreciated in FIGS. 10A-10C, the displacement sensor 410 may include a depth sensing arm 412 that may extend from the drill housing 26. For example, the depth sensing arm 412 may extend distally (e.g., from a distal face 30 of the drill housing 26) in a direction corresponding with the direction in which the drill bit 16 extends from a chuck 420 of the drill 50. At least a portion of the displacement sensing arm 412 may extend from the drill housing 26 parallel to an axis of rotation 120 of the drill 50. The depth sensing arm 412 may also include a distal portion 414 that is adapted to engage a bushing 452 provided with the drill bit assembly 60 shown in FIG. 12. In this regard, at least a portion of the depth sensing arm 412 (e.g., the distal portion 414) may be adapted to engage the bushing 452 of the drill bit assembly 60 as will be described in more detail below. At least a portion of the depth sensing arm 412 may extend into the housing 26. With further reference to FIG. 11, the housing 26 may contain a coil 416. As such, a proximal end 418 of the displacement sensing arm 412 may interface with the coil 416 of the displacement sensor 410 that may be disposed within the drill housing 26.

Specifically, in FIG. 11, the depth sensing arm 412 is shown in a retracted position relative to the drill bit 16. As such, this retracted position shown in FIG. 11 may occur when the drill bit 16 is advanced relative to the bushing 452 during drilling. In this regard, the proximal end 418 of the displacement sensing arm 412 is disposed within the coil 416 of the displacement sensor 410. Accordingly, the displacement sensor 410 may comprise an LVDT sensor as described above that is adapted to sense the position of a core 422 relative to a coil 416. The displacement sensing arm 412 may incorporate a core 422 at the proximal end 418 thereof. Accordingly, as the proximal end 418 of the displacement sensing arm 412 is moved relative to the coil 416, the location of the core 422 may be determined to provide an output corresponding to the position of the core 422, and in turn the displacement sensing arm 412 relative to the drill housing 26. That is, the depth sensing arm 412 may be displaceable relative to the coil 416 such that the displacement sensor 410 may be operable to sense a change in position of the depth sensing arm 412 relative to the drill housing 26 and output a measure of the displacement that may be used as described above in determining a depth of a bore. In an embodiment, the total measurable travel of the core 422 relative to the coil 416 may be at least about 2.5 in (6.4 cm). In other embodiments, the total measurable travel of the core 422 relative to the coil 416 may be at least about 0.5 in (1.27 cm), at least about 1 inch (2.54 cm), at least about 1.5 in (3.81 cm), at least about 2 in (5.08 cm), at least about 2.25 in (5.72 cm), at least about 2.75 in (6.99 cm), at least about 3 in (7.62 cm), or greater than 3 in (7.60 cm). Furthermore, the resolution of the output of the displacement sensor 410 may be about 0.1%.

In an embodiment, the coil 416 may define a passage 424 extending at least partially through the housing 26. Specifically, the passage 424 may extend from a proximal face 32 of the housing 26 to the distal face 30 of the housing 26. That is, the passage 424 may extend entirely though the housing 26. An end cap 34 may be provided that is operable to close the proximal end of the passage 424 at the proximal face 32 of the drill housing 26. Furthermore, a biasing member 426 (e.g., a coil spring) may be provided in the passageway 424 at a proximal end thereof. The biasing member 426 may be provided between the end cap 34 and the proximal end 418 of the displacement sensing arm 412. In this regard, the biasing member 426 may act on the proximal end 418 of the displacement sensing arm 412 to bias the displacement sensing arm 412 distally relative to the passage 424 and drill housing 26.

Figure 20:
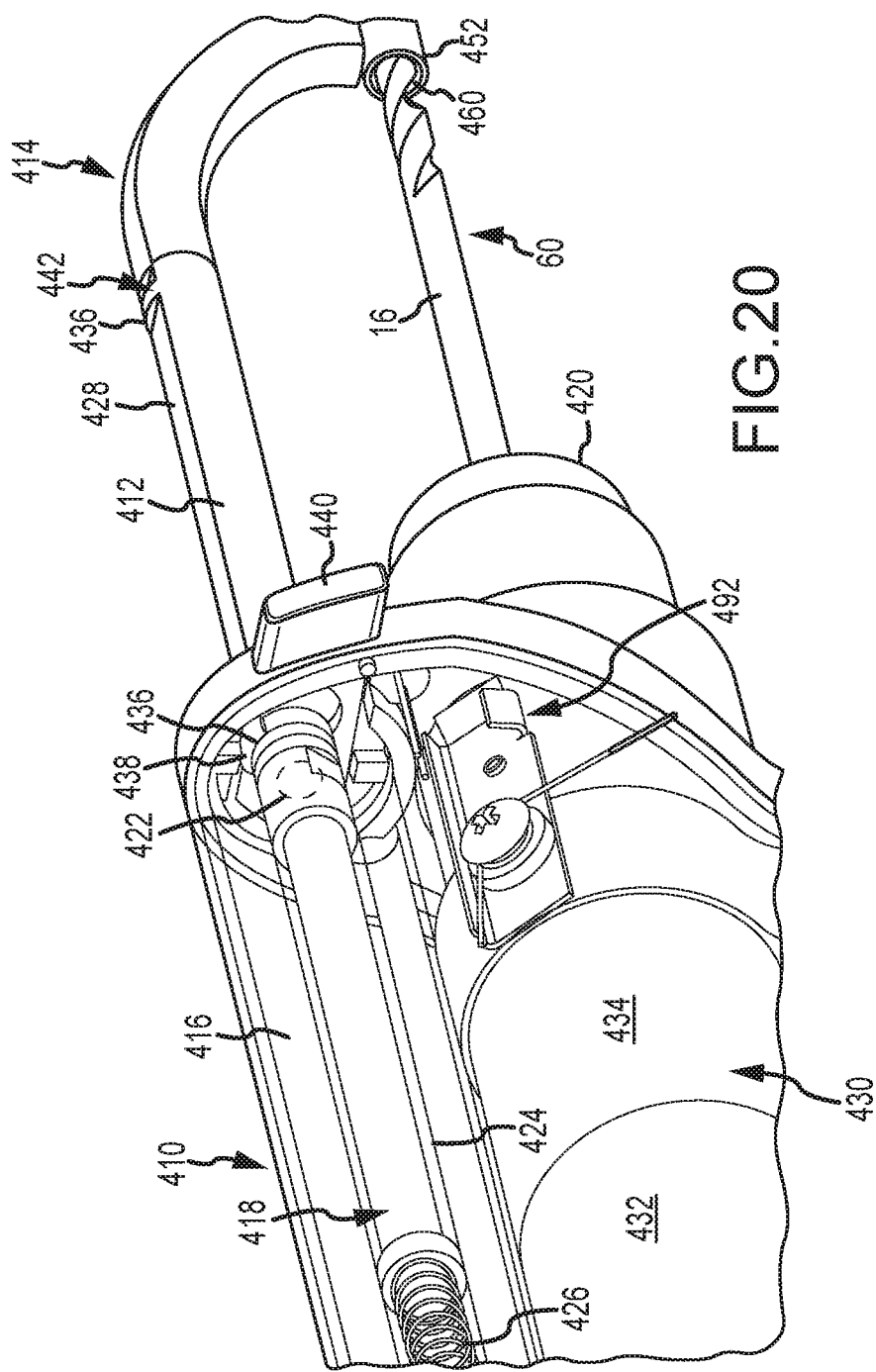
FIG. 20 is a perspective view in partial cutaway of an embodiment of a drill comprising a measurement system.

As such, the displacement sensing arm 412 may include features that selectively prevent ejection of the displacement sensing arm 412 from the distal end of the passage 424. For example, the displacement sensing arm 412 may include at least one flat 428 that extends along a portion of the arm 412. At the proximal and distal extents of the flat 428, the displacement sensing arm 412 may include shoulders 436 that project from the flats 428 (best seen at the distal portion 414 in FIG. 10B and at the proximal portion 418 in FIG. 11). As such, at the proximal opening of the passage 424, a selectively displaceable stop 438 (best seen in FIG. 20) may be disposed relative to the flat 428 such that the flat 428 may move relative to the stop 438, but interfere with the shoulder 436 defined in the displacement sensing arm 412 to prevent passage of the shoulder 436 beyond the stop 438. In this regard, the length of the displacement sensing arm 412 along which the flat 428 extends may be moveable relative to the stop 438, and the stop 438 may limit proximal and distal movement of the displacement sensing arm 412 beyond the stop 438.

However, the stop 438 may be displaceable upon depressing a button 440 provided on an exterior of the housing 26. Thus, upon depressing the button 440, the stop 438 may be displaced away from the displacement sensing arm 412 to allow the shoulder 436 to pass distally from the distal end of the passage 424 such that the displacement sensing arm 412 may be removed entirely from the passage 424. The distal end of the flats 438 may include a detent 442 that may be engageable with the stop 438 so as to maintain the displacement sensing arm 412 in a proximally disposed, retracted position relative to the housing (e.g., as shown in FIG. 11). Once the button 440 is depressed and released, the detent 442 at the proximal end of the flat 428 of the displacement sensing arm 412 may be released by the stop 438 and the displacement sensing arm 412 may move proximally (e.g., under influence of the biasing member 426). The displacement sensing arm 412 may move proximally until the shoulder 436 at the distal end of the flat 428 are engaged to prevent further distal movement of the displacement sensing arm 412. Accordingly, the displacement sensing arm 412 may be retained in a retracted position (e.g., for improved visibility of the distal end of the drill bit 16), released to be moveable relative to and biased proximally with respect to the housing 26, and removable altogether from the housing 26.

In the latter regard, removal of the displacement sensing arm 412 and biasing member 426 from the passage 424 may allow for separate cleaning (e.g., in an autoclave) of those members. Additionally, removal of the end cap 34 may allow for a cleaning apparatus (e.g., a brush or the like) to be passed through the full length of the passage 424 to facilitate cleaning thereof.

As referenced above, the distal portion 414 of the displacement sensing arm 412 may be adapted to engage a drill bit assembly 60 (e.g., a bushing 452 thereof) that is correspondingly adapted for use with the drill 50. For instance, as shown in FIGS. 10A-10C and FIG. 11, the displacement sensing arm 412 may generally be linear at the proximal portion 418. In this regard, the proximal portion 418 may be adapted to be collinear with the passage 424 and moveable within the passage 424. Furthermore, the distal portion 414 of the displacement sensing arm 412 (e.g., the portion distal to the linear portion of the displacement sensing arm 412) may extend from the linear portion of the displacement sensing arm 412 toward the drill bit assembly 60 that may be engaged by the chuck 420 of the drill 50. In this regard, the linear portion of the displacement sensing arm 412 may be substantially parallel to and offset from the axis of rotation 120. The distal portion 414 may extend from the linear portion in a direction corresponding with the offset such that the distal portion 414 extends toward the drill bit assembly 60. This may facilitate engagement between the displacement sensing arm 412 and the bushing 454 of the drill bit assembly 60.

Figure 12:
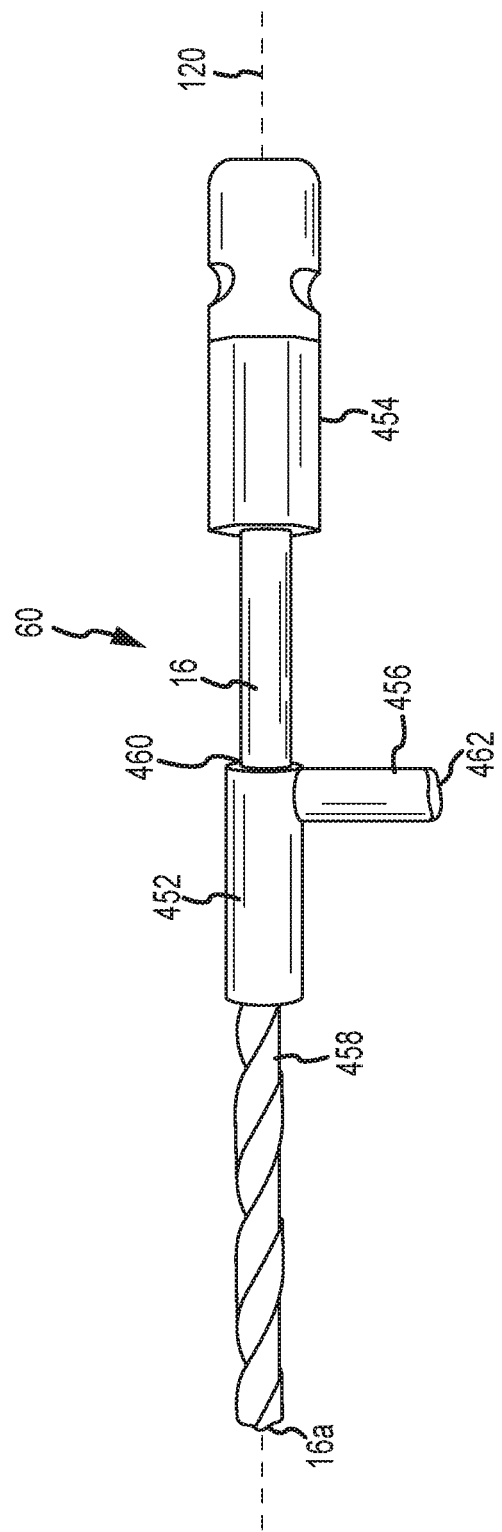
FIG. 12 is a side view of a drill bit assembly for use with an embodiment of a drill comprising a drill bit penetration measurement system.

With further reference to FIG. 12, an embodiment of a drill bit assembly 60 that may be used in conjunction with the drill 50 is depicted. The drill bit assembly 60 may include a shank 454 that is disposed adjacent to a proximal end of the assembly 60. Furthermore, the assembly 60 may comprise a leading edge 16a at the distal end thereof. The leading edge 456 may include a cutting edge that, when rotated serves to cut the medium into which the bit 16 is advanced as per a standard drill bit. A cylindrical member 458 (e.g., at least a portion thereof having flutes provided therein to remove cut material from the cutting edge) may extend between the shank 454 and the leading edge 456. The leading edge 456, cylindrical body 458, and shank 454 may collectively define the drill bit 16.

In addition to the drill bit 16, the drill bit assembly 60 may also comprise a bushing 452 as referenced above. The bushing 452 may engage the cylindrical member 458 to facilitate relative movement of the bushing 452 relative to the cylindrical member 458 along a direction corresponding to the axis of rotation 120. For example, the bushing 452 may include an aperture 460 through which at least a portion of the cylindrical member 458 may be disposed. The aperture 460 may form a cylindrical opening that extends at least in a direction corresponding to the axis of rotation 120 of the drill bit 16. The cylindrical opening may be sized to receive the cylindrical member 458 therein such relative movement between the cylindrical opening and the cylindrical member 458 is provided. As such, the drill bit 16 may be free to rotate within the aperture 460, and the bushing 452 may slideably engage the cylindrical member 458 for relative movement therebetween that is constrained along the direction corresponding to the axis of rotation 120.

The bushing 452 may include an engagement member 456 that is disposed on the bushing 452 and adapted for engagement with a displacement sensing arm 412 of a drill 50 to which the drill bit assembly 60 is engaged. For instance, as depicted in FIG. 12, the engagement member 456 may comprise a post 462 extending from the bushing 452. The post 462 may extend away from the axis of rotation 120 of the drill bit assembly 60. In an embodiment, the post 462 may extend perpendicularly to the axis of rotation 120. Accordingly, the post 462 may engage a hole 464 provided on the distal portion 414 of the displacement sensing arm 412. In this regard, the post 462 may extend into the hole 464. Movement of the bushing 452 relative to the drill bit 16 in a direction corresponding to the axis of rotation 120 may result in the post 462 acting on the hole 464 such that the displacement sensing arm 412 undergoes corresponding movement upon movement of the bushing 452 relative to the drill bit 16. In turn, as described above, the core 422 at the proximal portion 418 the displacement sensing arm 412 may also undergo corresponding movement relative to the coil 416, which may be detected by the displacement sensor 410 and output as a displacement measure.

It may be appreciated that other arrangements for engaging the bushing 452 with the displacement sensing arm 412 may be provided so that the bushing 452 and displacement sensing arm 412 undergo corresponding movement. For example, other structures such as clasps, fasteners, or other mechanisms may be utilized to engage the bushing 452 to the displacement sensing arm 412. Furthermore, the bushing 452 may, in some embodiments, be integrally defined on the distal portion 414 of the displacement sensing arm 412. In this regard, a standard drill bit 16 may be engaged with a chuck 420 of the drill 50 and the bushing 452 may be disposed relative to the bit 16. In any regard, the bushing 452 may be pivotal relative to the displacement sensing arm 412 (e.g., in a direction perpendicular to the axis of rotation 120) to facilitate ease of engagement of the bushing 452 with the displacement sensing arm 412 or the bushing 452 with the drill bit 16 when engaging the drill bit 16 with the chuck 420 of the drill 50.

Figure 17A:
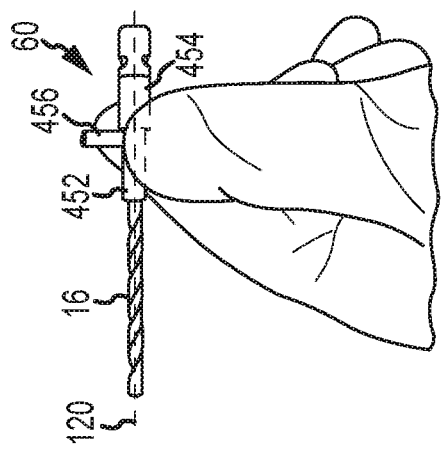
FIGS. 17A-17D depict a progression for engagement of a drill bit assembly with a drill having a drill bit penetration measurement system.
Figure 17B:
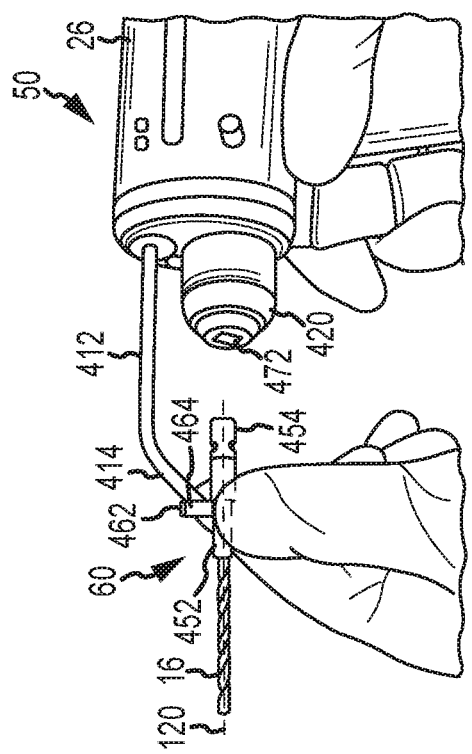
Figure 17C:
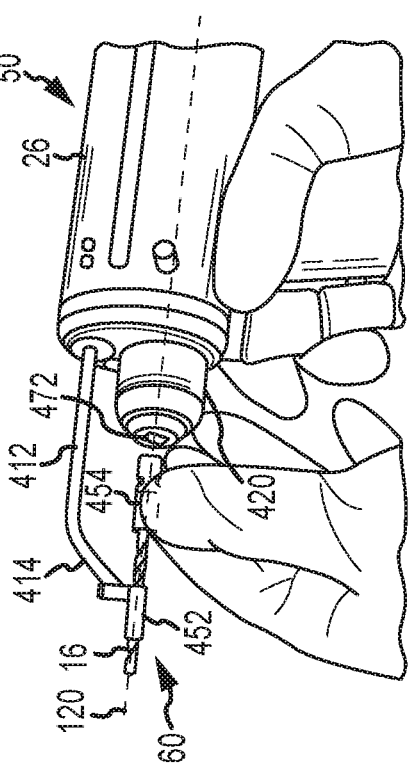
Figure 17D:
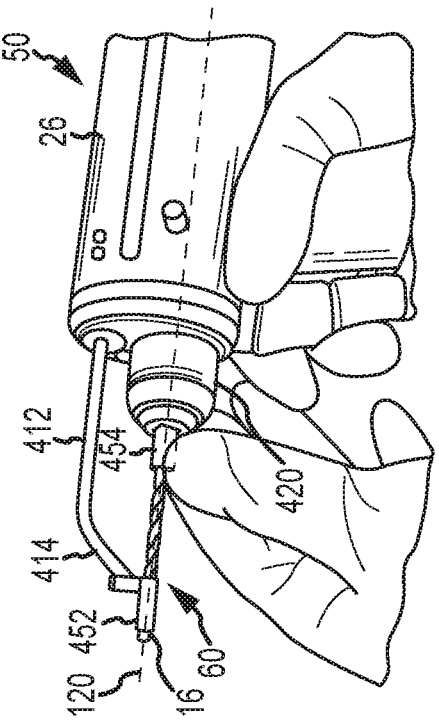

For example, with reference to FIGS. 17A-17D, a progression of images are shown that illustrate engagement of the drill bit assembly 60 with a drill 50. In FIG. 17A, the drill bit assembly 60 is grasped by a user at the bushing 452. Thereafter in FIG. 17B, the post 462 of the bushing 452 is disposed in a hole 464 of the displacement sensing arm 412 extending from the drill housing 26. As may be appreciated, given the cylindrical interface between the post 462 and the hole 464, the bushing 452 and drill bit 16 may still be rotatable perpendicularly to the axis of rotation 120. As such, the shank 454 may be aligned with the chuck 420 as shown in FIG. 17C. Thereafter, the drill bit 16 may be moved proximally such that the chuck 420 engages the shank 454. As shown and described in greater detail below, the chuck 420 may comprise a "quick-change" style chuck that allows for rapid insertion and removal of drill bits 16 therefrom. However, other types of chucks may be utilized without limitation such as, for example, a jawed chuck, a collet, a magnetic chuck, etc.

In any regard, the shank 454 of the drill bit assembly 60 may be engaged with the chuck 420 of the drill 50. In this regard, the drill bit 16 may be fixed relative to the drill 50 in the direction along the axis of rotation 120. In turn, the bushing 452 may be displaceable relative to the drill bit 16 along the axis of rotation 120. In this regard, when the drill bit 16 is advanced into a medium during a drilling operation, the bushing 452 may remain stationary at a reference point established prior to the drilling operation and the displacement sensor 410 may be operable to detect the relative motion between the drill bit 16 and the bushing 452 retained in a stationary position relative to the reference point, thus providing a measure of the relative movement of the drill bit 16 relative to the reference point.

Figure 19:
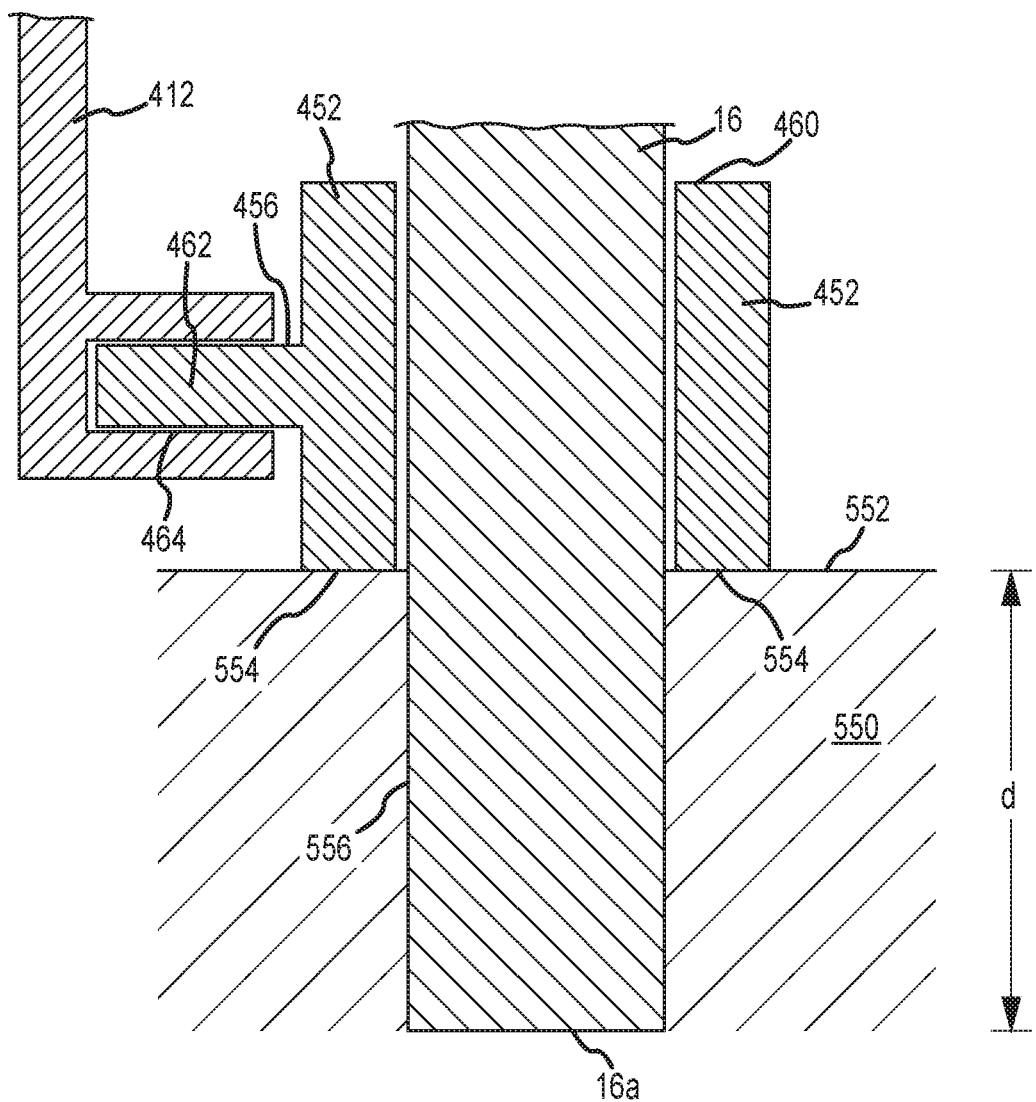
FIG. 19 is a cross sectional schematic view of a drill bit that has been advanced into a bore in a medium relative to a bushing engaged with a distal portion of a displacement sensing arm.

For instance, with further reference to FIG. 19, a schematic section view of a drill bit 16 that has been advanced into a medium 550 is shown. The bushing 452 may be disposed about the drill bit 16. As such, the bushing 452 may be disposed about the periphery of the bore 556 created upon advancement of the drill bit 16 into the medium 550. That is, the bushing 452 may remain in contact with the surface 552 of the medium 550 upon advancement of the drill bit 16 into the medium 550. In this regard, the bushing 454 may include a reference surface 554 at a distal portion thereof. The reference surface 554 may contact the surface 552 of the medium 550 to be drilled. As such, prior to initiation of the drilling when the leading edge 16a of the drill bit 16 is also in contact with the surface 552, the displacement sensor 410 may be set to establish the reference point. Accordingly, as the drill bit 16 is advanced, the reference surface 554 may remain in contact with the surface 552 of the medium 550. The reference surface 554 may contact the surface 552 about a periphery of the bore 556. In an embodiment, the reference surface 554 may extend circumferentially about a majority or substantially all of the drill bit 16 such that the reference surface 554 may also extend circumferentially about a majority of or substantially all of the periphery of the bore 556. The distally biased displacement sensing arm 412 may act on the bushing 452 (e.g., by way of post 462 received in hole 464) to maintain the bushing 452 in contact with the surface 552. In any regard, the displacement (d) of the leading edge 16a of the drill bit 16 relative to the reference surface 554 of the bushing 454 may be measured upon corresponding movement of the core 422 at the proximal end 418 of the displacement sensing arm 412 relative to the coil 416.

In this regard, measurement of the displacement of the leading edge 16a of the drill bit 16 relative to the reference surface 554 of the bushing 454 that is maintained against the surface 552 of the medium 550 to be drilled may provide improved accuracy regarding the displacement of the leading edge 16a into the bore 556. As described above, as the reference surface 554 is maintained in contact with the medium 550 adjacent to the periphery of the bore 556, there is less possibility for relative movement between the bushing 452 and the medium 550 that may introduce error into the measured displacement d. Furthermore, as the bushing 452 is in contact with the medium 550 adjacent to the bore 556, the contact with the patient required to obtain the measurement is lessened as the extension 110 may not need to contact the patient in a location away from the bore 556. Thus, the drilling operation is less invasive, thus improving patient outcomes.

A number of additional features may also be provided for the drill 50 and/or drill bit assembly 60 that are described in conjunction with the embodiment of the drill 50. It may be appreciated that these features may be provided with other types of drills and/or drill bit assemblies 60 and are not required to be used in conjunction with a drill 50 and drill bit assembly 60 incorporating features for coordinated operation between the displacement sensor 410 and drill bit assembly 60 as described above.

Figure 13:
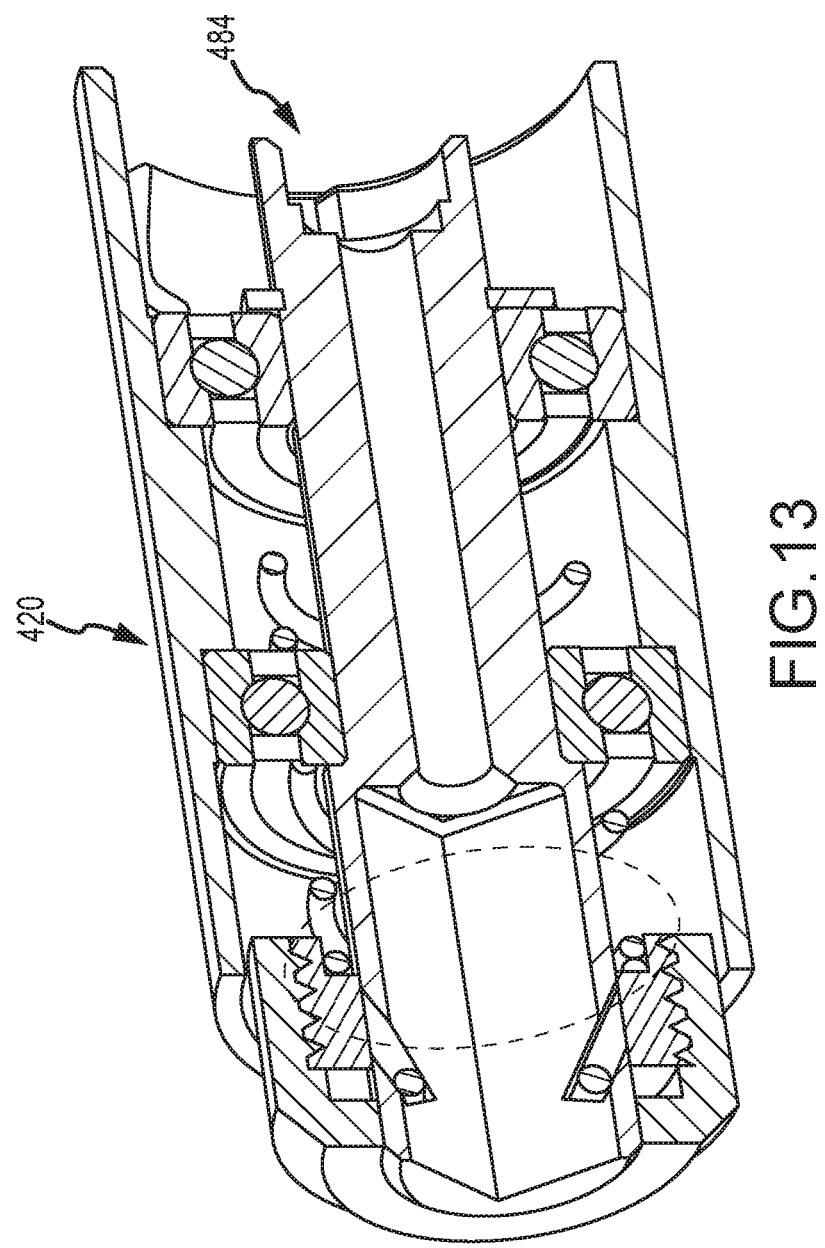
FIG. 13 is a perspective view in cross section of an embodiment of a chuck.
Figure 14:
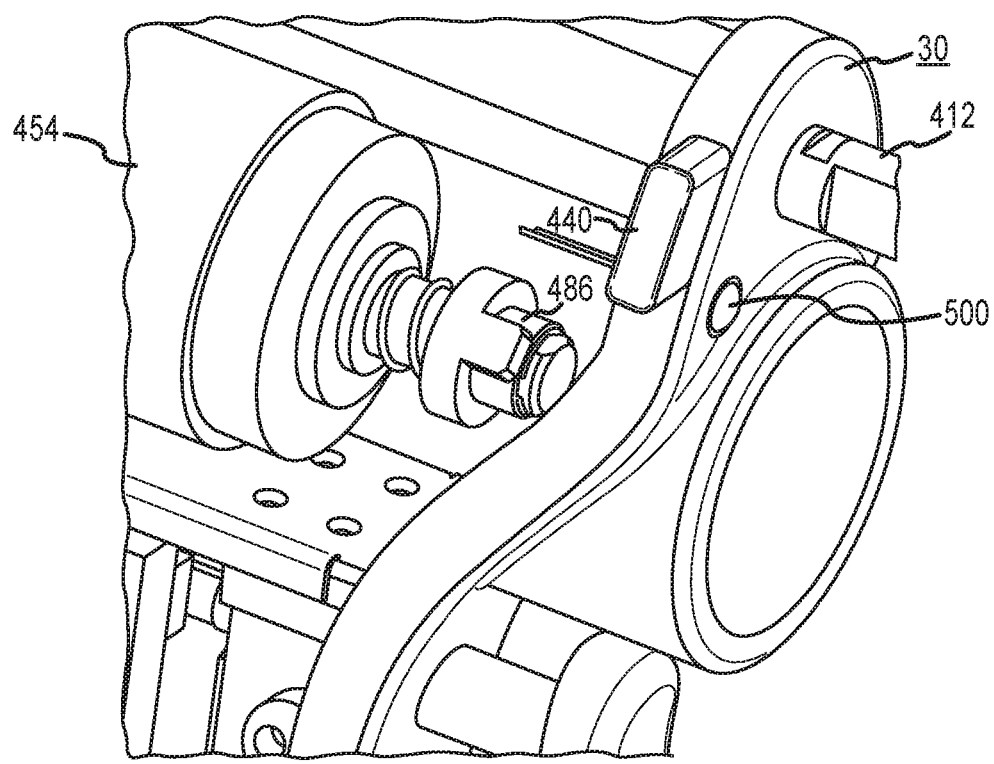
FIG. 14 is a cut away view showing an embodiment of a coupling of a drill that corresponds to the chuck of FIG. 15.

For instance, the drill 50 may include a removable chuck 420 that provides for quick interchange and/or removal of the chuck 420. As may further be appreciated from FIG. 11, the drill 50 may include a drive 430. The drive 430 may a motor 432 and gearbox 434. The drive 430 may engage a chuck 420. Specifically, the chuck 420 may be provided in removable engagement with the drive 430 such that the chuck 420 may be releasably engaged with the drive 420. As may be further appreciated in FIG. 13, the chuck 454 may include a chuck drive coupling 484 at a proximal end thereof. In this regard, as may be appreciated in FIG. 14, the drill 50 may include a corresponding drill drive coupling 486 that engages with the chuck drive coupling 484 to impart rotational motion from the drive 430 to the chuck 420. In this regard, the chuck 420 may be detachable from the drill 50.

Figure 15:
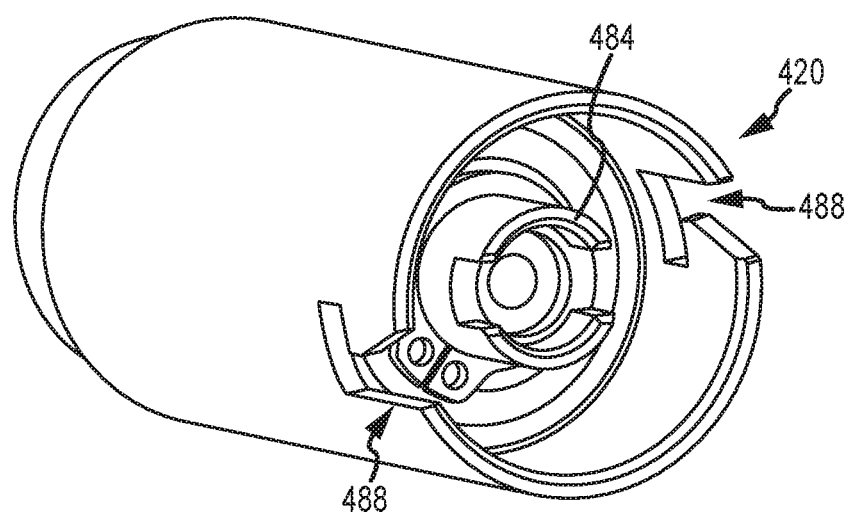
FIG. 15 is a perspective view of the proximal end of the chuck of FIG. 14.
Figure 16A:
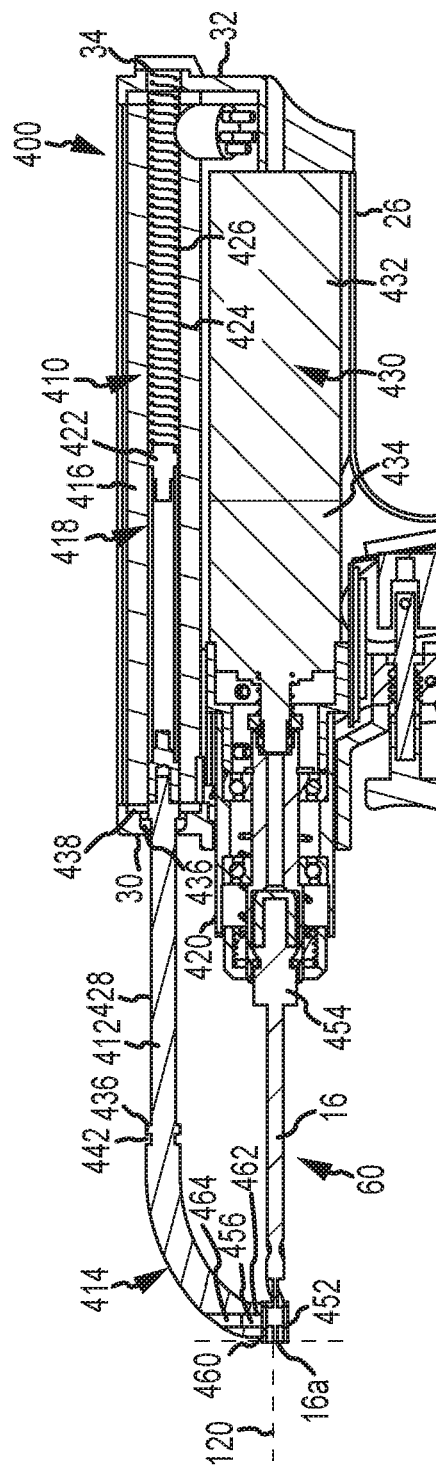
FIGS. 16A and 16B are cross sectional views of an embodiment of a drill comprising a drill bit penetration measurement system.
Figure 16B:
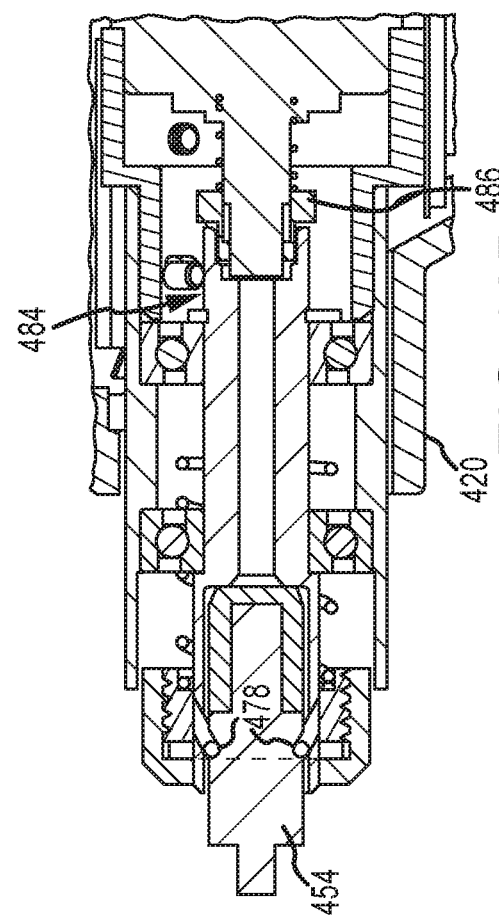

For instance, with further reference to FIG. 15, the proximal end of the chuck 420 may include slots 488 that may coordinate with corresponding tabs 490 (best seen in FIG. 16B) to retain the chuck 420 relative to the drill 50 such that the dill drive coupling 486 engages the chuck drive coupling 484 to impart rotational motion thereto. The slots 488 may coordinate with the tabs 490 so to allow the chuck 420 to be quickly attached and/or released from the drill 50 by engagement of the slots 488 with the tabs 490. The tabs 490 may be operatively engaged with a release 492. Accordingly, upon actuation of the release (e.g., from the exterior of the drill housing 26), the tabs 490 may disengage the chuck 420 to allow the chuck to be removed. Thus, the chuck 420 may be quickly and efficiently attached and detached from the drill 50. With further reference to FIGS. 16A and 16B, cross sectional views of the drill 50 with drill bit assembly 60 engaged therewith are shown. As may be appreciated, the drill drive coupling 486 may engage the chuck drive coupling 484. As may also be appreciated, the chuck 450 may be operatively engaged with the drill drive 430 such that the engagement of the slots 488 of the chuck 420 are engaged with the tabs 490 disposed relative to the drill body 26.

With specific reference to FIG. 16A, it may be appreciated that the bushing 452 of the drill bit assembly 60 may be engaged with the distal portion 414 of the displacement sensing arm 412. Accordingly, as may be appreciated, the drill bit 16 may be operatively engaged with the chuck 420 so as to limit relative movement therebetween along the axis of rotation 120 such that relative movement between the bushing 452 and displacement sensing arm 412 may be sensed as described above.

The drill may also include a light emitter 500 disposed on a distal face 30 of the drill hosing 26. In this regard, the light emitter 500 may be operable to emit light in a direction toward the drill bit 16 when engaged with the chuck 420. As such, the light emitter 500 may illuminate at least a portion of the drill bit 16 during the drilling operation to improve visibility of the medium being drilled. The light emitter 500 may comprise a light source such as, for example, an incandescent bulb, a light emitting diode (LED), a laser source, or other light source known in the art. Alternatively, a light source may be disposed remotely from the light emitter 500 and the light may be transmitted from the remote light source to the light emitter 500 using optical elements such as fiber optics or the like.

Figure 21:
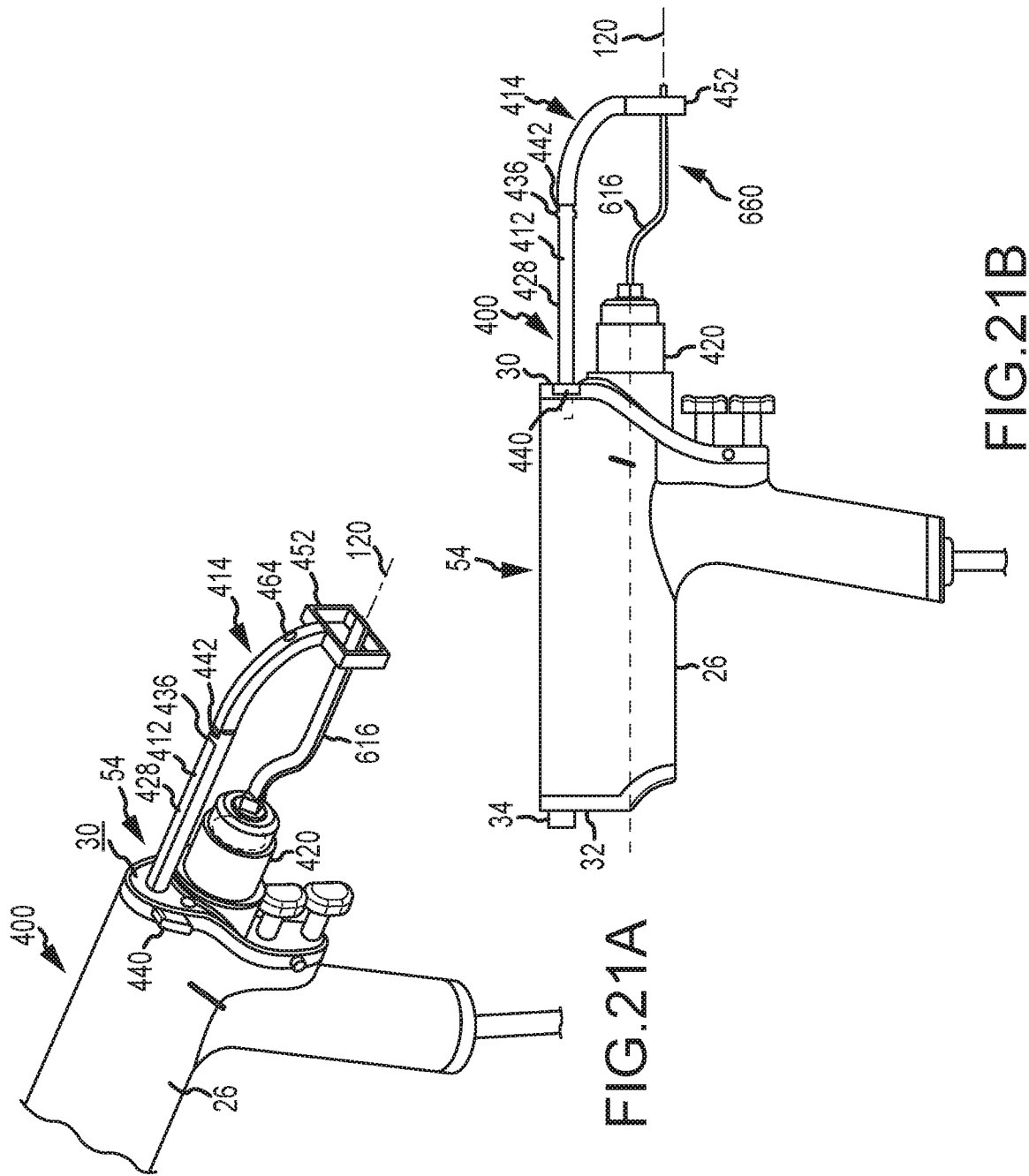
FIGS. 21A and 21B are a perspective and side views, respectively, of an embodiment of a saw comprising a measurement system.

As discussed above, the foregoing may also apply to other powered instruments such as saws, burr reamers, etc. For example, with additional reference to FIGS. 21A and 21B, an embodiment of a saw 54 with a measurement system 400 is shown. The saw 54 may incorporate at least some features described above in relation to the context of a drill 50. As such, like elements are referred to with the same numerals in the following description. For example, at least a portion of a displacement sensor 410 may be integrated into a housing 26 of the saw 54. In this regard, the displacement sensor 410 may include a depth sensing arm 412 that is specifically adapted for engagement with a bushing 452 of a saw blade assembly 660 that may be engaged by the chuck 420 of the saw 54.

In this regard, the depth sensing arm 412 may be used to establish a reference point from which displacement of the saw blade 616 may be measured as described above. In this regard, as follows herein, a general description of the features and operation of the saw 54 used in conjunction with the saw blade assembly 660 is provided.

The saw blade assembly 660 may include a shank that is disposed adjacent to a proximal end of the assembly 660. Furthermore, the assembly 660 may include a cutting edge at the distal end thereof. The cutting edge may include a cutting edge that, when oscillated, serves to cut the medium into which the blade 616 is advanced as per a standard saw blade. The direction in which the saw blade is advanced during a cutting operation may be referred to as a cutting direction 120 that is generally orthogonal to the cutting edge. A blade member may extend between the shank and the cutting edge. The cutting edge, body, and shank may collectively define the saw blade 616.

In addition to the saw blade 616, the saw blade assembly 660 may also include a bushing 452 as referenced above. The bushing 452 may engage the blade member to facilitate relative movement of the bushing 452 relative to the blade member along a direction corresponding to the cutting direction 120. For example, the bushing 452 may include an aperture through which at least a portion of the blade member may be disposed. The aperture may form an opening that extends at least in a direction corresponding to the cutting direction 120 of the saw blade 616. The opening may be sized to receive the blade member therein such relative movement between the opening and the blade member is provided. As such, the saw blade 616 may be free to oscillate within the aperture, and the bushing 452 may slideably engage the member for relative movement therebetween that is constrained along the direction corresponding to the cutting direction 120.

Figure 25:
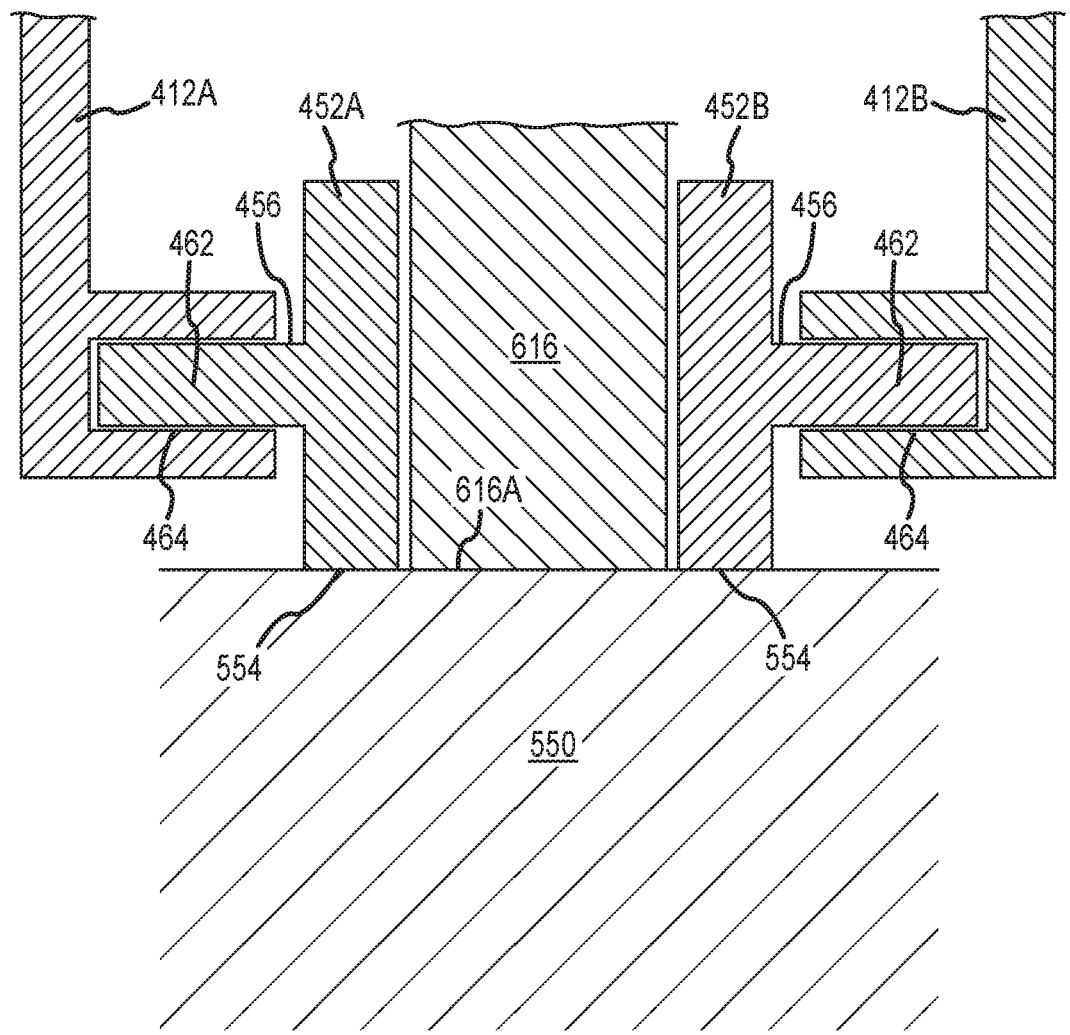
FIGS. 25 and 26 are cross-sectional schematic views of an embodiment of a saw blade used in conjunction with a plurality of depth sensing arms.

The bushing 452 may include an engagement member that is disposed on the bushing 452 and adapted for engagement with a displacement sensing arm 412 of a saw 54 to which the saw blade assembly 660 is engaged. For instance, the engagement member may include a post 456 extending from the bushing 452 (FIG. 25). The post may extend away from the cutting direction 120 of the saw blade assembly 660. In an embodiment, the post may extend perpendicularly to the cutting direction 120. Accordingly, the post may engage a hole provided on the distal portion of the displacement sensing arm 412. In this regard, the post may extend into the hole. Movement of the bushing 452 relative to the saw blade 616 in a direction corresponding to the cutting direction 120 may result in the post acting on the hole such that the displacement sensing arm 412 undergoes corresponding movement upon movement of the bushing 452 relative to the saw blade 616. In turn, as described above, the core at the proximal portion the displacement sensing arm 412 may also undergo corresponding movement relative to the coil 416, which may be detected by the displacement sensor 410 and output as a displacement measure.

It may be appreciated that other arrangements for engaging the bushing 452 with the displacement sensing arm 412 may be provided so that the bushing 452 and displacement sending arm 412 undergo corresponding movement. For example, other structures such as clasps, fasteners, or other mechanisms may be utilized to engage the bushing 452 to the displacement sensing arm 412. Furthermore, the bushing 452 may, in some embodiments, be integrally defined on the distal portion 414 of the displacement sensing arm 412. In this regard, a standard saw blade 616 may be engaged with a chuck 420 of the saw 50 and the bushing 452 may be disposed relative to the blade 616. In any regard, the bushing 452 may be pivotal relative to the displacement sensing arm 412 (e.g., in a direction perpendicular to the cutting direction 120) to facilitate ease of engagement of the bushing 452 with the displacement sensing arm 412 or the bushing 452 with the saw blade 616 when engaging the saw blade 16 with the chuck 420 of the saw 54.

Figure 22:
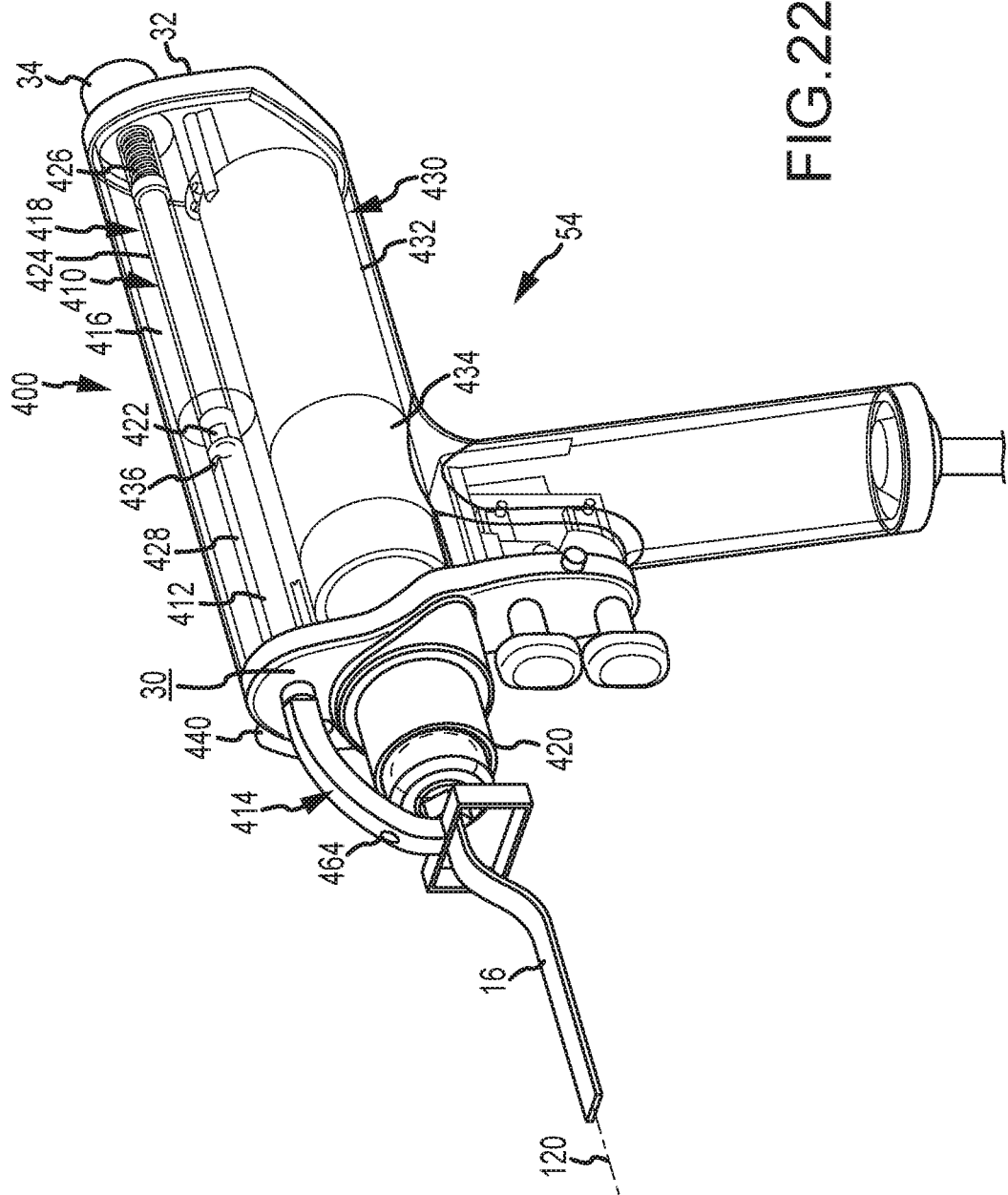
FIG. 22 is a perspective view in partial cutaway of an embodiment of a saw comprising a measurement system.
Figure 23:
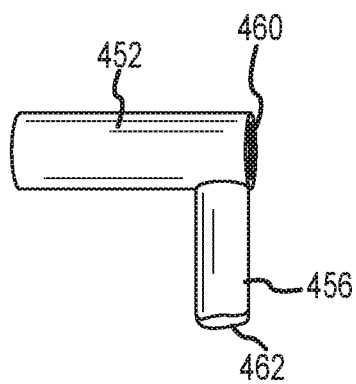
FIG. 23 is a side view of an embodiment of a bushing for use with a saw.
Figure 24:
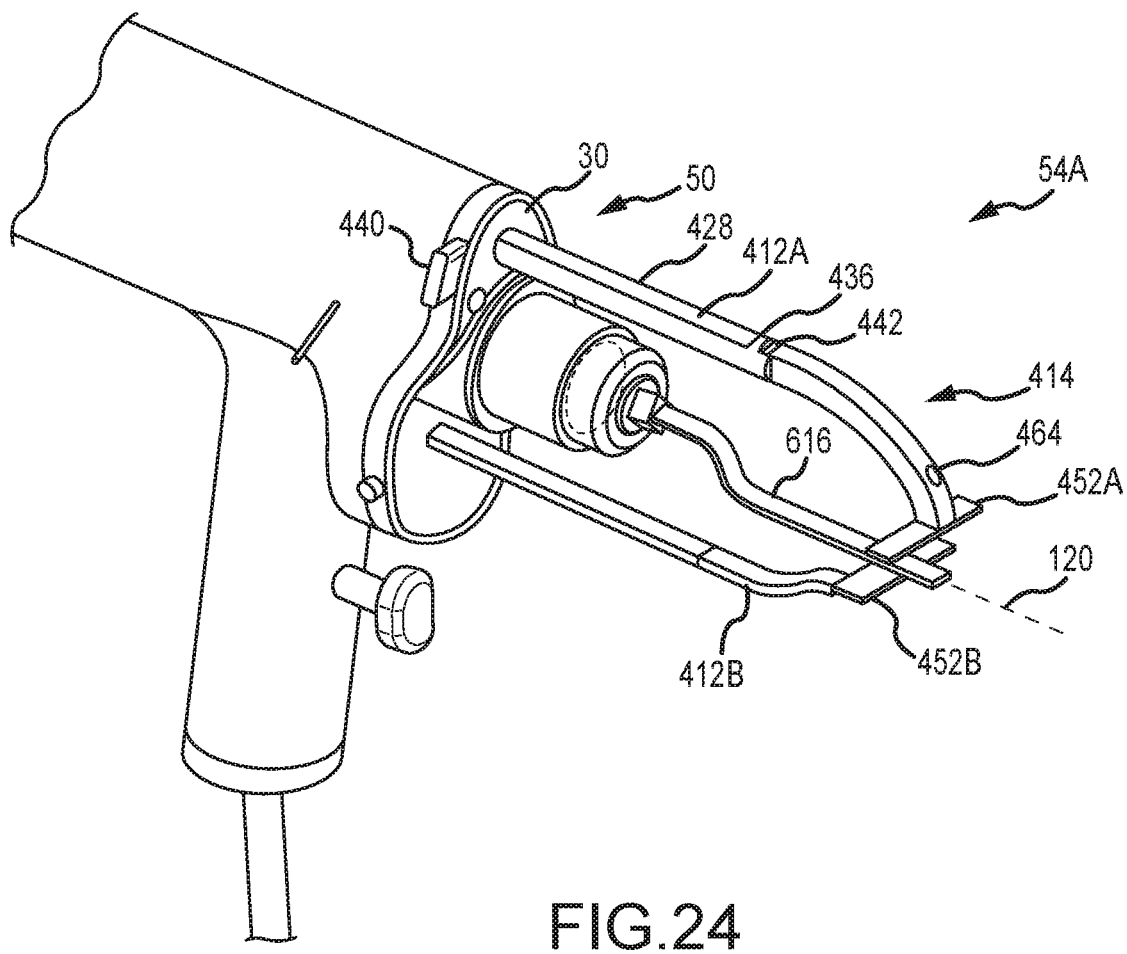
FIG. 24 is a perspective view of an embodiment of a saw having a plurality of depth sensing arms.

As shown in FIG. 24, an embodiment of a saw 54A with two measurement systems is shown. Displacement sensors similar to the displacement sensor 410 of FIGS. 21A-22 may be integrated into a housing of the saw 54A. In this regard, the displacement sensors may each include a depth sensing arm 412A and 412B, respectively, that is specifically adapted for engagement with a corresponding bushing 452A or 452B. In this regard, the depth sensing arms 412A and 412B may be used to establish reference points from which displacement of the saw blade 616 may be measured as described above.

The displacement sensors may include depth sensing arms 412A or 412B that may extend from the saw housing. For example, the depth sensing arms 412A and 412B may extend distally (e.g., from a distal face 30 of the saw housing) in a direction corresponding with the direction in which the saw blade 616 extends from a chuck of the saw 54A. At least a portion of the displacement sensing arms 412A or 412B may extend from the saw housing along the length of the saw blade 616 of the saw 54A. The depth sensing arms 412A and 412B may also include a distal portion 414 that is adapted to engage a bushing 452A or 452B, respectively. As used herein, distal may correspond to a direction from the saw 54A toward the cutting edge of the saw blade 616 and proximal may correspond to a direction from the cutting edge of the saw blade 616 toward the saw 50A. In this regard, at least a portion of the depth sensing arms 412A or 412B (e.g., the distal portion 414) may be adapted to engage the bushings 452A and 452B of the saw blade assembly. In any regard, at least a portion of the depth sensing arms 412A and 412B may extend into the housing. The housing of the saw 54A may contain components for both of the sensing arms 412A and 412B that are shown within the housing 26 of FIG. 24. As such, a proximal end of the displacement sensing arm 412B also interfaces with a coil of a displacement sensor that may be disposed within the saw housing as described above in relation to depth sensing arm 412.

Figure 26:
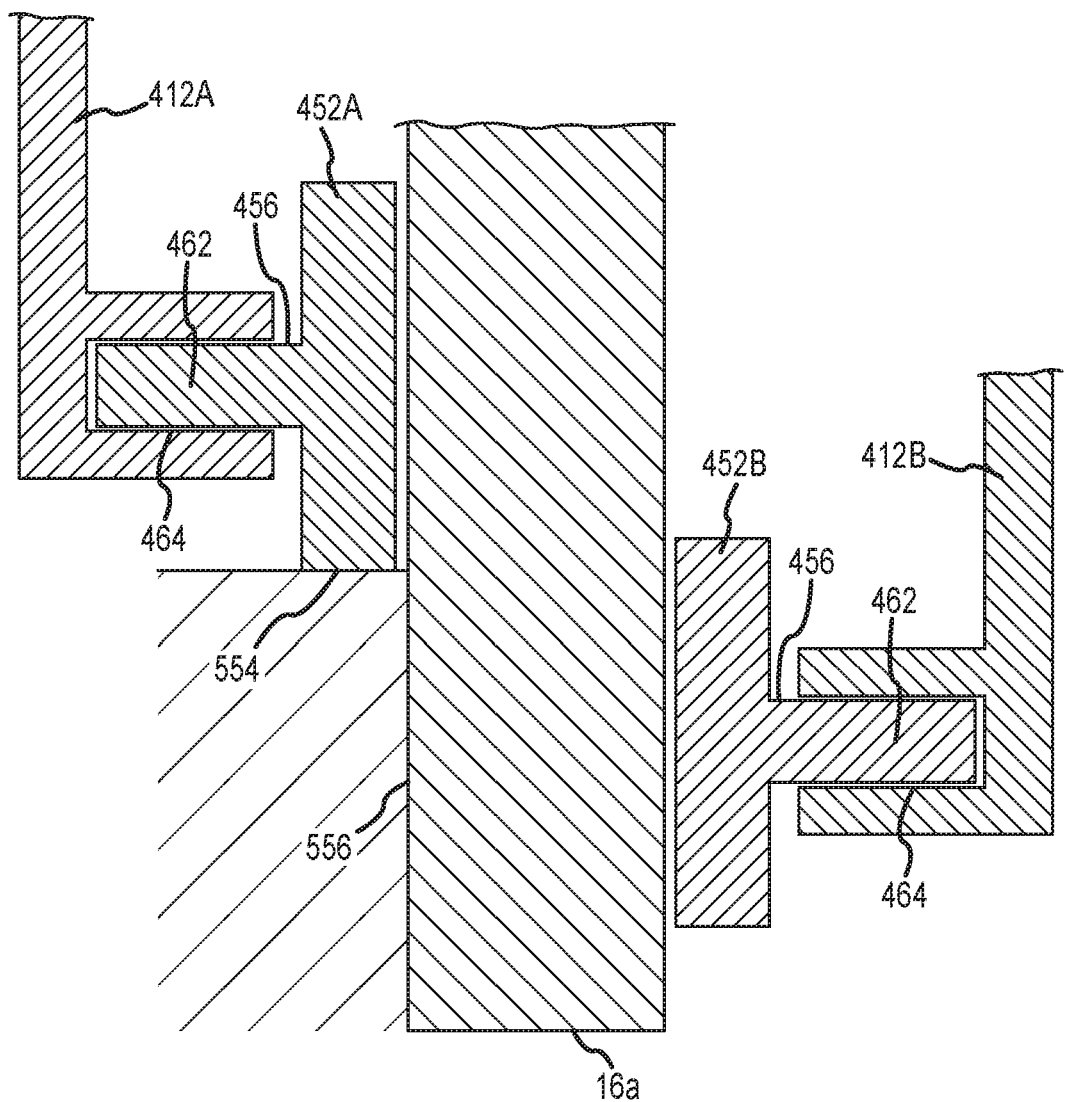

FIG. 25 presents a cross sectional view of the initiation of a cut using a saw 54A having depth sensing arms 412A and 412B. FIG. 26 shows when the cut has been completed and one side of the medium 550 has been dislodged. This causes one of the bushings 452B to release due to a lack of counter force from the medium 550. When this occurs the processor will receive a signal from the position sensor associated with the second bushing 452B that is different from a signal from the position sensor associated with the first bushing 452A. In one embodiment, the processor will generate a signal indicating that the cut is complete when the signals from the two position sensors differ by greater than a previously defined threshold amount. This generated signal causes an automatic slowing of motion or stopping altogether of the saw motor. An output device may generate an alert (visual, tactile or audible) for a saw user based on the generated cut completion signal.

FIG. 27 shows the saw 54 used with an exemplary cutting guide/jig 480. In one embodiment, the cutting guide/jig 480 is U-shaped for receiving a portion of a patient's anatomy. The cutting guide/jig 480 includes two opposing walls. The walls include slot guides 482 that receive the saw blade 616. The slot guides 482 can be thin enough to act as bearing members to the received saw blade 616 without cause undue friction during oscillation of the saw blade. As the saw blade 616 is received within the slot guides 482 a displacement sensing arm 412 uses the side of the cutting guide/jig 480 as a reference surface. Thus, the cutting block 480 may receive the saw blade in the slot guides 482 to direct the saw blade relative to the patient's anatomy. The displacement sensing arm 412 and related components (processor) generate a cutting depth value that takes into consideration the thickness of the wall of the cutting guide/jig 480—provided the item being cut maintains contact with the interior wall of the cutting guide/jig 480. Furthermore, the displacement sensing arm 412 may contact a portion of the cutting block 480 that is stationary relative to the anatomy to be cut rather than the anatomy itself.

In one embodiment, the cutting guide/jig 480 is adjustable for allowing different sized patient parts to be received. Also, the height, depth and width of the slot guides 482 is also adjustable for accepting different size and time type of cutting blades (e.g., reciprocating, ultrasonic, etc.) Also, guide(s) separate from or attachable to the cutting guide/jig 480 provide barriers for guiding motion of the housing of the saw in a desired cutting direction.

Figure 29:
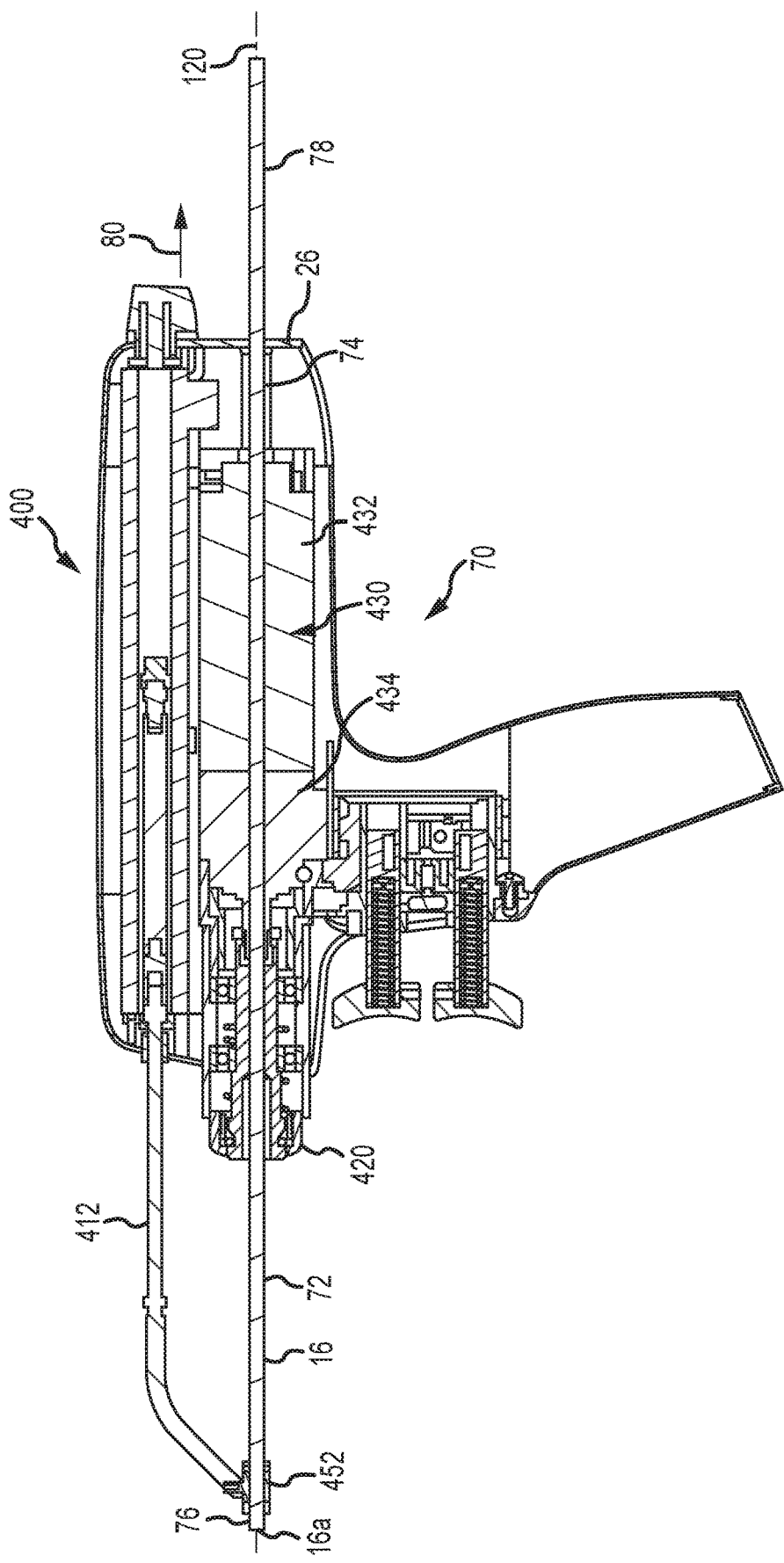
FIGS. 29 and 30 depict an embodiment of a cannulated drill.
Figure 30:
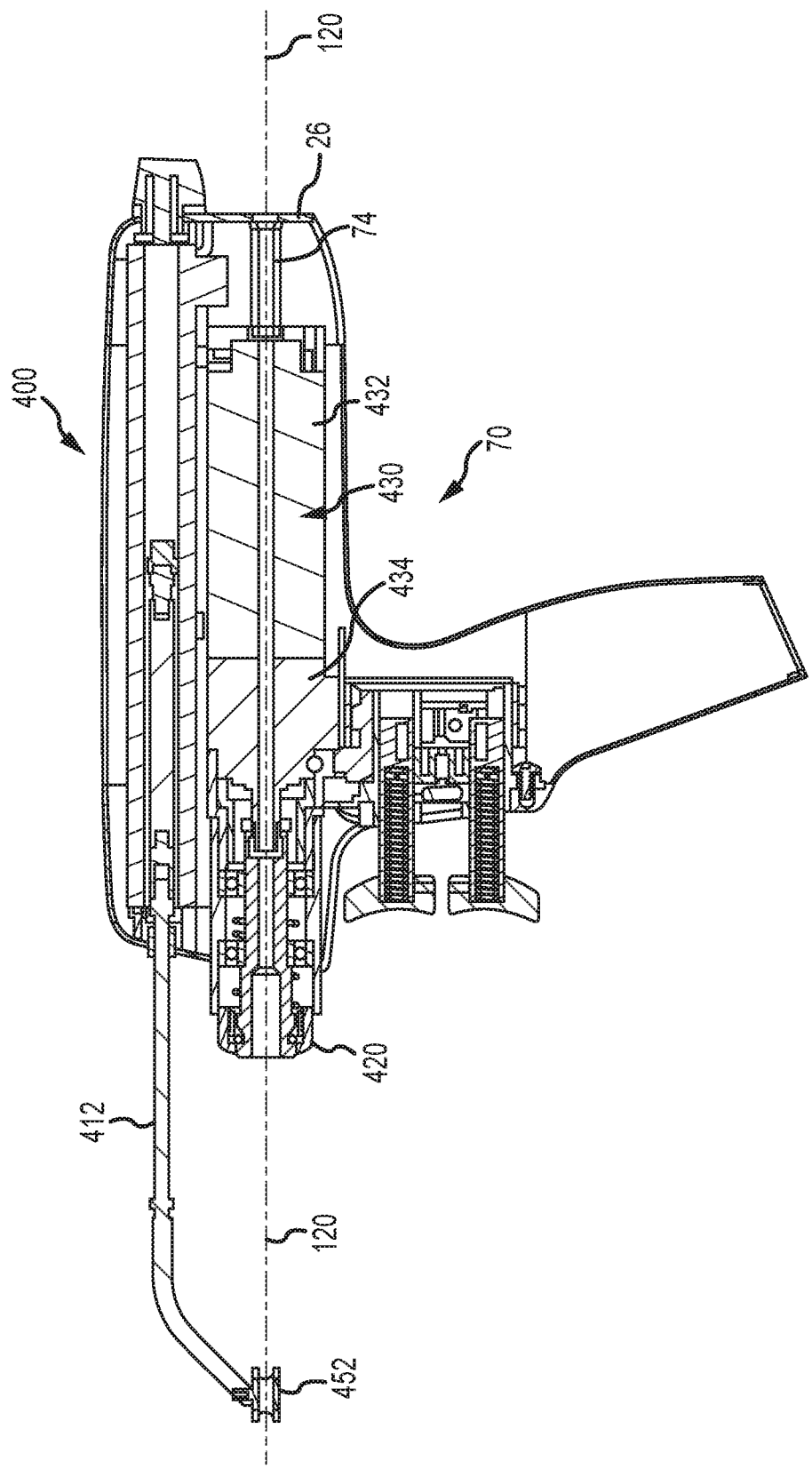

As described above, in certain embodiments the instrument 16 may include a transcutaneous pin that is placed relative to bone 10. In this regard, an embodiment of a drill 70 for placement of such a transcutaneous pin 72 is depicted in FIGS. 29 and 30. Use of the drill 70 in relation to the transcutaneous pin 72 may allow for placement of the pin 72 relative to a given structure of a bone 10. The pin 72 may be secured by a drill 70 that is cannulated. With further reference to FIG. 30, the cannula 74 may extend along the entire length of the drill 70 along the axis of rotation 120 of the drill 70. In this regard, the cannula 74 may extend through the chuck 420, and drive 430. Furthermore, the cannula 74 may also extend through the distal portion of the drill housing 26 such that the cannula 74 may receive the transcutaneous pin 72 as shown in FIG. 29. In turn, the pin 72 may be secured by the drill 70 (e.g., by the cannulated chuck 420) thereof such that the drill 70 may impart rotational movement to the pin 72. The pin 72 may have a distal portion 76 that allows for the pin 72 to both cut through and anchor into a portion of the structure of the bone 10. In this regard, it may be desirable to have the distal portion 76 of the pin 72 enter the second portion 12b of the hard outer cortex 12, yet not pass all the way therethrough. The drill 70 may be operated to advance the distal portion 76 of the pin 72 into the second portion 12b of hard outer cortex 12, at which time an occurrence signal 148 may be generated. In response, an alert may be provided to the surgeon to arrest the drill 70 (e.g., an auditory alert or an automatic arresting of the drill 70 may occur in response to the occurrence signal 148). In turn, the pin 72 may be released from the drill 70 (e.g., the chuck 420 thereof) and the drill 70 may be slidingly removed from a proximal end 78 of the pin 72 in the direction of arrow 80 such that the pin 72 passes through the cannula 74 in the drill 70 and is removed proximally from the pin 72 that is secured in the bone 10. In turn, the placement of the transcutaneous pin 72 may be assisted as the distal portion 76 of the pin 72 may be advanced to a desired portion with the assistance of the measurement system 100.

With further reference to FIGS. 31A-33B, various embodiments of an instrument guide 82 housing a displacement sensor for use in conjunction with an instrument 16 are depicted. In FIG. 31A the instrument guide 82 includes a body 84. The body 84 may include a cylindrical opening 85 through which the instrument 16 may pass. The body 84 may extend at least partially about the instrument 16. For instance, the instrument guide 82 may surround the instrument 16 circumferentially about a majority of or substantially all of the instrument 16. The body 84 may include a plunger 86 that is moveable with respect to the body 84. For example, the plunger 86 may be biased by a biasing member 88 toward a chuck member 420 that retains the instrument 16. In this regard, when the instrument 16 is advanced relative to a medium 550, the plunger 86 may be depressed with respect to the body 84, thus compressing the biasing member 88. The relative movement of the plunger 86 with respect to the body 84 may be detected such that the displacement of the leading edge 16a of the instrument 16 may be detected. For instance, the movement of the plunger 86 with respect to the body 84 may be detected using an LVDT sensor as described above.

The instrument guide 82 may further include a clamping member 96. As shown in FIG. 31A, the clamping member 96 may be recessed within the cylindrical opening 85. However, upon detection of an occurrence of the leading edge 16a passing from a first medium to a second medium, the clamping member 96 may be deployed for clamping engagement with respect to the instrument 16. In this regard, in the case of a rotational instrument 16, the clamping member 96 may clampingly engage the instrument 16 to arrest the instrument 16 or at a minimum reduce the speed thereof. As such, the clamping member 96 may be deployed to arrest or slow the instrument 16 at the occurrence of the leading edge 16a passing from a first medium to the second medium.

Figure 32B:
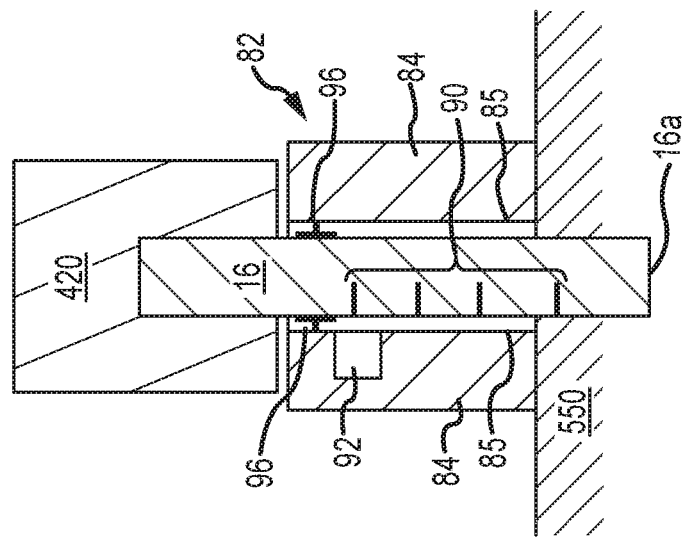
Figure 32A:
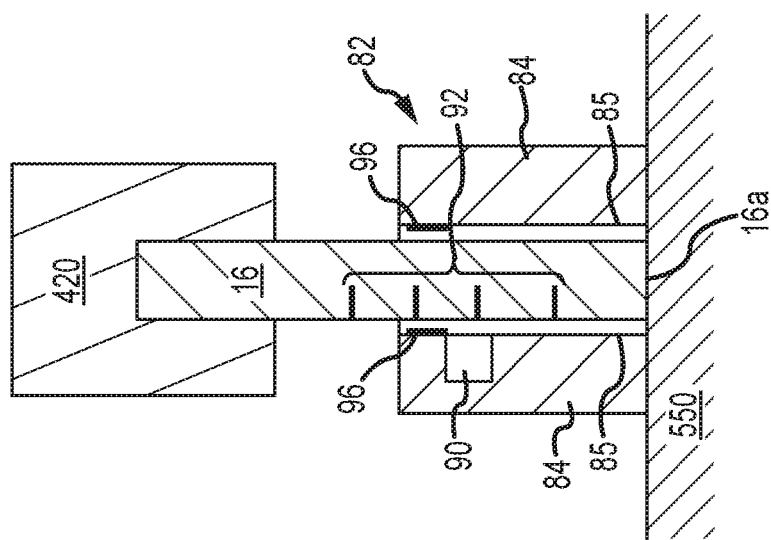

FIGS. 32A and 32B depict another embodiment of an instrument guide 82 where like reference numerals are used for like elements as those discussed above in reference to FIGS. 31A and 31B. In FIGS. 32A and 32B, the instrument guide 82 may include an optical sensor 90 disposed within a body 84. The instrument 16 may include markings 92 disposed on the instrument 16. In this regard, the optical sensor 90 may be operative to sense the markings 92 to determine a displacement signal of the instrument 16 is advanced relative to the medium 550.

Figure 33B:
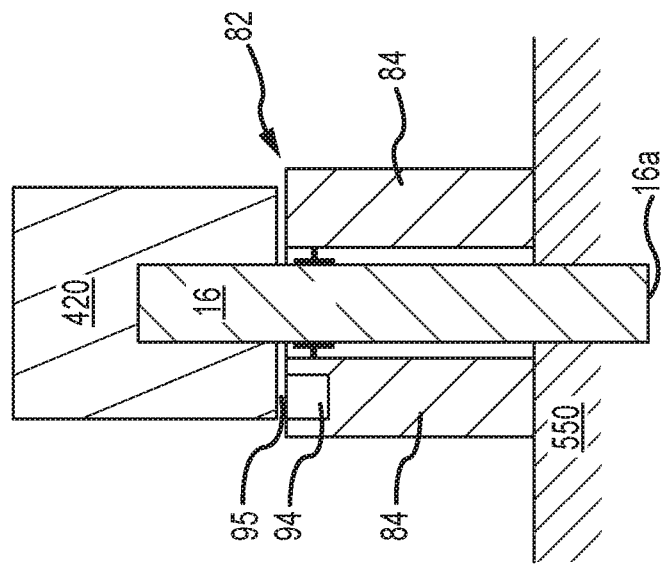
Figure 33A:
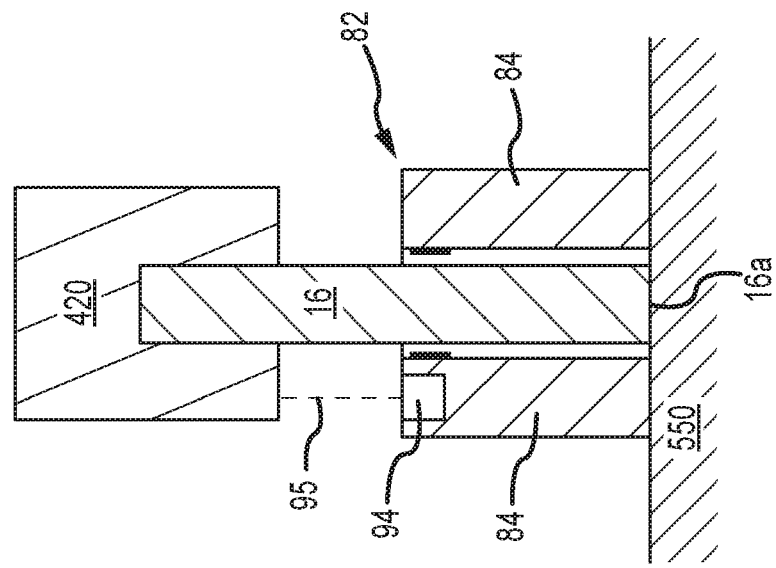

In FIG. 33A and FIG. 33B, the instrument guide 82 may include a laser sensor 94. The laser sensor 94 may project a laser beam 95 towards the chuck 420 such that the length of the laser beam 95 may be measurable. In this regard, as the instrument 16 is advanced relative to the medium 550 as shown in FIG. 33B, the displacement of the instrument 16 relative to the instrument guide 82 may be determined to generate a displacement signal.

In each of FIG. 31A to FIG. 33B, the instrument guide 82 may be disposed adjacent to the medium 550 into which the instrument 16 is advanced. In this regard, the instrument guide 82 may be maintainable engageable against a peripheral portion about a portion of the medium 550 through which the instrument 16 is advanced. Accordingly, the instrument guide 82 may define a reference point relative to the medium in a direction along an axis of advancement of the instrument 16. For instance, the instrument guide 82 may be engageable with a fixture, plate, or other structure affixed or disposed relative to the medium 550 on which the instrument 16 is to be used. As may be appreciated, the instrument guide 82 may be completely separate from the instrument 16 such that a traditional instrument 16 may be utilized in conjunction with instrument guide 82 such that the benefits described above related to the termination of an occurrence of the leading edge 16a of the instrument 16 passing from a first medium to a second medium may be realized. Accordingly, the instrument guide 82 may be in operative communication with a controller as described above (e.g., by wireless or wired means).

Those skilled in the art will appreciate that changes could be made to the embodiments described above without departing from the broad inventive concept thereof. It is understood, therefore, that this invention is not limited to the particular embodiments disclosed, but it is intended to cover modifications within the spirit and scope of the present invention as defined by the appended claims.

What is claimed is:

1. A method for determining an occurrence of when a leading edge of an instrument passes from a first medium to a second medium contiguous with the first medium, wherein the first medium has a first density and the second medium has a second density, the method comprising:
   outputting from a displacement sensor disposed within an instrument housing a displacement signal corresponding to movement of the leading edge of the instrument relative to a reference point in response to a displacement sensing arm undergoing relative movement to the displacement sensor upon the displacement of the leading edge of the instrument relative to the reference point;
   generating a velocity signal by calculating a first derivative of the displacement signal with respect to time and an acceleration signal by calculating a second derivative of the displacement signal with respect to time; and
   determining an occurrence of the leading edge of the instrument passing from the first medium to the second medium based only on the displacement signal, the velocity signal, and the acceleration signal.

2. The method of claim 1, wherein the occurrence of the leading edge of the instrument passing from the first medium to the second medium is determined when the displacement signal is positive, the velocity signal is positive, and the acceleration signal is positive.

3. The method of claim 2, wherein the determining further comprises determining the occurrence of the leading edge of the instrument passing from the first medium to the second medium at an occurrence of the displacement signal exceeding a predetermined displacement signal value, the velocity signal exceeding a predetermined velocity signal value, and the acceleration signal each exceeding a predetermined acceleration signal value.

4. The method according to claim 1, further comprising:
   generating an alert upon the occurrence of the leading edge of the instrument passing from the first medium to the second medium.

5. The method according to claim 4, wherein the alert is perceivable by a user of the instrument.

6. The method according to claim 5, wherein the alert is an auditory alert.

7. The method according to claim 5, wherein the generating the alert comprises changing an angular velocity of the instrument.

8. The method according to claim 7, wherein the generating the alert comprises stopping rotation of the instrument.

9. The method according to claim 8, wherein the outputting is in response to the instrument passing through an instrument guide disposed about at least a portion of the instrument.

10. The method according to claim 9, wherein the stopping comprises applying a clamping force on the instrument by the instrument guide.

11. The method according to claim 1, further comprising:
measuring, with respect to a reference point, a depth of penetration of the leading edge of the instrument at the occurrence of the leading edge of the instrument passing from the first medium to the second medium.

12. The method of claim 11, further comprising:
outputting an indication of the depth of penetration of the leading edge of the instrument at the occurrence of the leading edge of the instrument passing from the first medium to the second medium.

13. The method according to claim 1, further comprising:
applying a filter such that the occurrence cannot occur within a predetermined amount of time subsequent to another occurrence.

\* \* \* \* \*